United States Patent [19]
Töpfer et al.

[11] Patent Number: 6,103,520
[45] Date of Patent: *Aug. 15, 2000

[54] PLANT DNA ENCODING GLYCEROL-3-PHOSPHATE DEHYDROGENASE (GPDH)

[75] Inventors: Reinhard Töpfer, Bergheim; Lüdger Hausmann; Jozef Schell, both of Köln, all of Germany

[73] Assignee: Max-Planck-Gesellschaft zur Forderung der Wissenschaften E.V., Munich, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 08/605,150
[22] PCT Filed: Sep. 2, 1994
[86] PCT No.: PCT/EP94/02936
§ 371 Date: Jun. 19, 1996
§ 102(e) Date: Jun. 19, 1996
[87] PCT Pub. No.: WO95/06733
PCT Pub. Date: Mar. 9, 1995

[30] Foreign Application Priority Data

Sep. 3, 1993 [DE] Germany ............... 43 29 827

[51] Int. Cl.⁷ ............................................. C12N 15/82
[52] U.S. Cl. ............... 435/320.1; 536/23.2; 536/23.6; 536/24.1
[58] Field of Search ............... 536/23.1, 23.2, 536/23.6, 24.1; 435/320.1, 252.3, 69.1, 172.3, 419, 468, 469, 470; 800/200, 205, 295, 298, 278, 281

[56] References Cited

PUBLICATIONS

Stitt et al., Regulation of metabolism in transgenic plants, Annu. Rev. Plant Physiol. Plant Mol. Biol., vol. 46, pp. 341–368, 1995.

Bewley GC, et al. "Sequence, structure and evolution of the gene coding for sn–glycerol–3–phosphate dehydrogenase in Drosophila melanogaster." Nucl. Acids Res. 17: 8553–8567, 1989.

Stam M, et al. "The silence of genes in transgenic plants." Ann. Bot. 79: 3–12, 1997.

Koziel MG, et al. "Optimizing expression of transgenes with an emphasis on post–transcriptional events." Plant Mol. Biol. 32: 393–405, 1996.

Smith CJS, et al. "Antisense RNA inhibition of polygalacturonase gene expression in transgenic tomatoes." Nature 334: 724–726, Aug. 25, 1988.

Weising et al. (1988) *Annu. Rev. Genet.* 22:421–77.

Chan et al. (1993) *Plant Molecular Biology* 22:491–506.

Hooykaas and Schilperoot (1992) *Plant Molecular Biology* 19:15–38.

Schaläppi and Hohn (1992) *The Plant Cell* 4:7–16.

Klee et al. (1987) *Ann. Rev. Plant Physiol* 38:467–86.

Fromm et al. (1990) *Bio/Technology* 8:833–839.

Koziel et al. (1993) *Bio/Technology* 11:194–200.

Gordon–Kamm et al. (1990) *The Plant Cell.* 2:603–618.

Spencer et al. (1990) *Theor Appl Genet.* 79:625–631.

Conner and Dommisse (1992) *Int. J. Plant Sci.* 53/4:550–555.

Wilmink et al. (1992) *Plant Cell Reports.* 11:76–80.

*Primary Examiner*—Amy J. Nelson
*Attorney, Agent, or Firm*—Klein & Szekeres, LLP

[57] ABSTRACT

This invention discloses isolated DNA sequences encoding a glycerol-3-phosphate dehydrogenase, particularly DNA sequences isolated from *Cuphea lanceolata*. The invention also describes genomic clones from *Cuphea lanceolata* which contain the complete gene for glycerol-3-phosphate dehydrogenase including promoter sequences. The DNA sequences and clones of the invention are useful for the production of transgenic plants.

8 Claims, 6 Drawing Sheets

FIG. 1A

```
                                                                                              50
C1GPDH30   .........M  APSELNCTHQ  NPHSSGYDGP  RSRVTVVGSG  NWGSVAAKLI
C1GPDH109  .........M  APSELNSAHQ  NPHSSGYDGP  RSRVTVVGSG  NWGSVAAKLI
C1GPDHg3   MAPAFEPHQL  MSPAFEPHQQ  KP...TMENM  RFRVTIIGSG  NWGSVAAKLI
MmGPDH     ..........  ..........  .......MA   GKKVCIVGSG  NWGSATAKIV 51                                                                                100
C1GPDH30   ASNTLKLPSF  HDEVRMWVFE  ETLPSGEKLT  DVINQTNENV  KYLPGIKLGR
C1GPDH109  ASNTLKLPSF  HDEVRMWVFE  ETLPSGEKLT  DIINQTNENV  KYLPGIKLGG
C1GPDHg3   ASNTLNLPSF  HDEVRMWVFE  ETLPGGEKLT  EVINRTNENV  KYLPGFKLGR
MmGPDH     GSNAGRLAHF  DPRVTMWVFE  EDI.GGRKLT  EIINTQHENV  KYLPGHKLPP 101                                                                               150
C1GPDH30   NVVADPDLEN  AVKDANMLVF  VTPHQFMEGI  CKRLVGKIQE  GAQALSLIKG
C1GPDH109  NVVADPDLEN  AVKDANMLVF  VTPHQFMEGI  CKRLVGKIQE  GAQALSLIKG
C1GPDHg3   NVIADPNLEN  AVKFANMLVF  VTPHQFVEGL  CKRLVGKIKA  GAFALSLIKG
MmGPDH     NVVAIPDVVQ  AATGADILVF  VVPHQFIGKI  CDQLKGHLKA  NTIGISLIKG 151                                                                               200
C1GPDH30   MEVKMEGPCM  ISSLISDLLG  INCCVLMGAN  IANEIAVEKF  SEATVGFREN
C1GPDH109  MEVKMEGPCM  ISSLISDLLG  INCCVLMGAN  IANEIAVEKF  SEATVGFREN
C1GPDHg3   MEVKREGPSM  ISTLISSLLG  INCCVLNGAN  IANEIALEKF  SEATVGYREN
MmGPDH     VDEGPNGLKL  ISEVIGERLG  IPMSVLMGAN  IASEVAEEKF  CETTGCKDP
```

FIG. 1B

```
           201                                                                              250
C1GPDH30   TDIAEKWVQL  FSTPYFMVSA  VEDVEGVELC  GTLKNIVAIA  AGFVDGLEMG
C1GPDH109  RDIAEKWVQL  FSTPYFMVSA  VEDVEGVELC  GTLKNIVAIA  AGFVDGLEMG
C1GPDHg3   KDTAEKWVRL  FNTPYFQVSS  VQDVEGVELC  GTLKNVVAIA  AGFVDGLEMG
MmGPDH     AQ.GQLLKDL  MQTPNFRITV  VQEVDTVEIC  GALKNIVAVG  AGFCDGLGFG 251                                                                              300
C1GPDH30   NNTKAAIMRI  GLREMKAFSK  LLFPS.VKDT  TFFESCGVAD  LITTCLGGRN
C1GPDH109  NNTKAAIMRI  GLREMKAFSK  LLFPS.VKDT  TFFESCGVAD  LITTCKGGRN
C1GPDHg3   NNTKAAI...  ..........  ..........  ..........  ..........
MmGPDH     DNTKAAVIRL  GLMEMIAFAK  LFCSGTVSSA  TFLESCGVAD  LITTCYGGRN 301                                                                              350
C1GPDH30   RKVAEAFAKN  GGERSFDDLE  AELLRGQKLQ  GVSTAKEVYE  VLGHRGWLEL
C1GPDH109  RKVAEAFAKN  GGNRSFDDLE  AEMLRGQKLQ  GVSTAKEVYE  VLRHRGWLEL
C1GPDHg3   ..........  ..........  ..........  GVLTAKEVYE  VLKHRGWLER
MmGPDH     RKVAEAFART  G..KSIEQLE  KEMLNGQKLQ  GPQTARELHS  ILQHKGLVDK 351                                                              383
C1GPDH30   FPLFSTVHEI  STGRLHPSAI  VEYSEQKTIF  SW..
C1GPDH109  FPLFSTVHEI  SSGRLPPSAI  VEYSEQKPTF  SW..
C1GPDHg3   FPLFATVHEI  SSGRLPPSAI  VKYSEQKPVL  SRG.
MmGPDH     FPLFTAVYKV  CYEGQPVGEF  IRCLQNHPEH  M...
```

PLANT DNA ENCODING GLYCEROL-3-PHOSPHATE DEHYDROGENASE (GPDH)

BACKGROUND OF THE INVENTION

This invention concerns DNA sequences that code for a glycerol-3-phosphate dehydrogenase (GPDH) and the alleles as well as the derivatives of these DNA sequences.

This invention also concerns genomic clones that contain the complete gene of a glycerol-3-phosphate dehydrogenase and alleles as well as derivatives of this gene.

This invention also concerns promoters and other regulator elements of glycerol-3-phosphate dehydrogenase genes.

Glycerol-3-phosphate dehydrogenase (GPDH; EC 1.1.1.8), also known as dihydroxyacetone phosphate reductase, is substantially involved in triacylglyceride biosynthesis in plants by supplying glycerol-3-phosphate. Fatty acid biosynthesis and triacylglyceride biosynthesis can be regarded as separate biosynthesis pathways owing to compartmentalization but as one biosynthesis pathway from the standpoint of the end product. De novo biosynthesis of fatty acids takes place in the plastids and is catalyzed by three enzymes or enzyme systems, i.e., (1) acetyl-CoA carboxylase (ACCase), (2) fatty acid synthase (FAS), and (3) acyl-[ACP]-thioesterase (TE). The end products of this reaction sequence in most organisms are either palmitic acid, stearic acid, or after desaturation, oleic acid.

In the cytoplasm, however, triacylglyceride biosynthesis takes place via the so-called "Kennedy pathway" in the endoplasmic reticulum from glycerol-3-phosphate which is made available by the activity of glycerol-3-phosphate dehydrogenase (S. A. Finnlayson et al., Arch. Biochem. Biophys., 199 (1980) pages 179–185), and from fatty acids present in the form of acyl-CoA substrates.

Probably the first discovery of the enzymatic activity of glycerol-3-phosphate dehydrogenase in plants involved potato tubers (G. T. Santora et al., Arch. Biochem. Biophys., 196 (1979) pages 403–411). This activity had not been observed in other plants before then (B. König and E. Heinz, Planta, 118 (1974) pages 159–169), so the existence of the enzyme had not been detected. Thus the formation of glycerol-3-phosphate on the basis of the activity of a glycerol kinase was discussed as an alternative biosynthesis pathway. Santora et al., loc. cit., subsequently detected GPDH in spinach leaves and succeeded in increasing the concentration of the enzyme approximately 10,000 times. They determined the native molecular weight to be 63.5 kDa and found the optimum pH for the reduction of dihydroxyacetone phosphate (DHAP) to be 6.8 to 9.5 for the reverse reaction. GPDH was likewise detected in Ricinus endosperm (Finlayson et al., Biochem. Biophys. 199 (1980) pages 179–185). According to more recent works (Gee et al., Plant Physiol. 86 (1988a) pages 98–103), two GPDH activities could be detected in enriched fractions, a cytoplasmic fraction (20–25%) and a plastid (75–80%). The two forms are regulated differently. Thus, for example, the cytoplasmic isoform can be activated by F2,6DP, while the plastid isoform is activated by thioredoxin (R. W. Gee et al., Plant Physiol., 86 (1988) pages 98–103 and R. W. Gee et al., Plant Physiol., 87 (1988) pages 379–383).

The methods of molecular biology are making increasing entry into plant cultivation practice. Changes in biosynthesis output with the formation of new components and/or higher yields of these components can be achieved with the help of gene manipulation, e.g., transfer of genes which code for enzymes. As one of the most important enzymes of triacylglyceride synthesis, GPDH has a significant influence on the oil yield of plants.

SUMMARY OF THE INVENTION

It is thus the object of this invention to improve the oil yield of crop plants by influencing the triacylglyceride content.

This object is achieved with the DNA sequences and the genes from the gethomic clones in accordance with the invention.

This invention concerns DNA sequences that code for a glycerol-3-phosphate dehydrogenase, and alleles as well as derivatives of these DNA sequences.

This invention also concerns genomic clones that contain a complete gene of a glycerol-3-phosphate dehydrogenase including the structure gene, the promoter and other regulator sequences, and alleles as well as derivatives of this gene.

This invention likewise concerns the promoters and other regulator elements of glycerol-3-phosphate dehydrogenase genes from the specified genomic clones, and the alleles as well as derivatives of these promoters.

This invention additionally concerns a method of producing plants, plant parts and plant products in which the triacylglyceride content or fatty acid content is altered, where DNA sequences or genes are transferred from the genomic clones by the methods of genetic engineering.

This invention also concerns the use of said DNA sequences or one of the genes originating from said genomic clones for altering the triacylglyceride content or its fatty acid pattern in plants.

Finally, this invention concerns transgenic plants, plant parts and plant products produced according to the aforementioned method.

The figures serve to clarify the present invention.

BRIEF DESCRIPTION OF THE DRAWINGS

FIG. 1: Comparison of the derived amino acid sequences SEQ ID NOS:8 and 4 respectively of the ClGPDH30 SEQ ID NO:7 and CLGPDH109 SEQ ID NO:3 cDNAs as well as the amino acid sequence SEQ ID NO:12 from the gene from the ClGPDHg3 (SEQ ID NO:11) genomic clone with the GPDH amino acid sequence of the mouse (Mm GPDH) SEQ ID NO:17;

DESCRIPTION OF THE INVENTION

Figure 2:
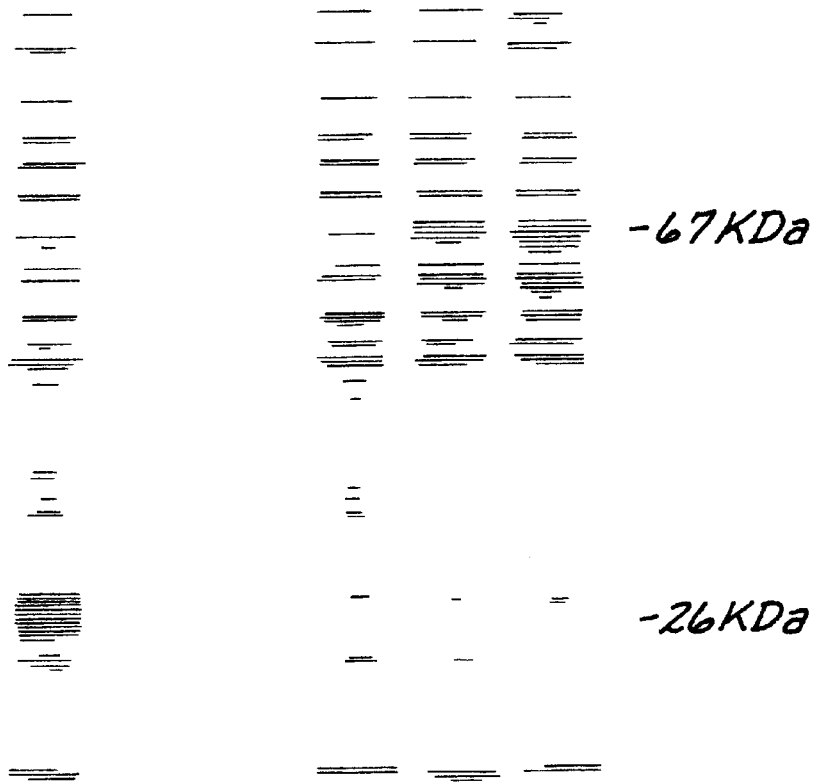
FIG. 2: Separation of proteins from BB26-36 cells by gel electrophoresis.

It follows that allelic variants and derivatives of DNA sequences or genes according to this invention are included within the scope of this invention under the assumption that these modified DNA sequences or modified genes will code for glycerol-3-phosphate dehydrgenase. The allelic variants and derivatives include, for example, deletions, substitutions, insertions, inversions and additions to DNA sequences or genes according to this invention.

Any plant material that produces glycerol-3-phosphate dehydrogenase in sufficient quantities is a suitable raw material for isolating cDNAs that code for glycerol-3-phosphate dehydrogenase. Isolated embryos from the plant *Cuphea lanceolata*, indigenous to Central America, have proven to be an especially suitable raw material in the present invention.

Functional complementation was used for isolation of DNA sequences according to this invention. This refers to complementation of mutant microorganisms with heterologous cDNA. Functional complementation was performed after infecting *E. coli* strain BB26-36, which is auxotrophic for glycerol, with phagemids containing plasmids with cDNAs from *Cuphea lanceolata*. Plasmids isolated from functionally complemented bacteria were cleaved with restriction endonucleases and separated by electrophoresis. The cDNAs contained in the plasmids were classified in two classes that differ in the size of their insertions. Retransformation confirmed that the isolated cDNAs were capable of complementing the BB26-36 mutant.

The complete coding area of one of the two classes codes for a glycerol-3-phosphate dehydrogenase contained in the ClGPDH20 cDNA clone. This is an Eco RI-ApaI fragment that has 1354 base pairs. The complete 1354 base pair DNA sequence of the ClGPDH20 cDNA and the amino acid sequence derived from it are entered in the Sequence Listing as SEQ ID NO:1. ClGPDH20 cDNA was sequenced double stranded. Proceeding from the ATG start codon, the cDNA codes from positions 17 to 1132 for a protein with 372 amino acids SEQ ID NO:1 (ending at the TAG stop codon), which is expressed as a fusion with lacZ without a shift in the reading frame. The estimated molecular weight is 40.8 kDa. Two base pairs (CA) preceding ATG are included with the cDNA. The first 14 nucleotides are attributed to the DNA sequence of the fusion with lacZ, and the linker sequence is indicated at the 3' end. The polyA signal is found at positions 1329 to 1334 in the 3' untranslated region.

It is assumed that ClGPDH20 cDNA SEQ ID NO:1 is a cytoplasmic isoform, because no transit peptide can be detected in homology comparisons with mouse GPDH SEQ ID NO:17 (see FIG. 1). On the basis of the position of an assumed NADH binding site corresponding to the consensus sequence GxGxxG (see positions 29 to 34 in the ClGPDH20 amino acid sequence in FIG. 1 (R. K. Wierenga et al., Biochem. 24 (1985) pages 1346–1357), the N-terminal sequence of 28 amino acids is not sufficient to code for a transit peptide whose length varies between 32 and 75 amino acids (Y. Gavel et al., FEBS Lett. 261 (1990) pages 455–458).

A cDNA library from *Cuphea lanceolata* was screened with ClGPDH20 cDNA SEQ ID NO:1 as a probe for isolation of additional GPDH cDNAs, and a total of 52 cDNA clones were isolated. The 18 longest cDNAs were completely or partially sequenced. The ClGPDH109, ClGPDH30 and ClGPDH132 cDNA clones contain cDNAs with the complete coding region or a virtually complete cDNA of GPDH.

The ClGPDH109 cDNA clone contains the complete coding region of GPDH on a 1464 base pair EcoRI-ApaI DNA fragment which codes for a protein with 381 amino acids. The DNA sequence is SEQ ID NO:3, and the amino acid sequence derived from it is shown as SEQ ID NO:4 in the Sequence Listing. The DNA fragment was sequenced double stranded. The coding area begins with the ATG start codon in position 45 and ends in position 1187, followed by the TAG stop codon (positions 1188 to 1190). The cDNA itself begins at position 15. The first 14 nucleotides are attributed to the DNA sequence of the fusion with lacZ. The polyA signal (positions 1414 to 1419) and the polyA area (positions 1446 to 1454) as well as the linker sequence (positions 1459 to 1464) are found in the untranslated region at the 3' end.

Another cDNA, ClGPDH30, also contains the complete coding region of GPDH on a 1390 base pair EcoRI-XhoI fragment, which codes for a protein with 372 amino acids. The double-stranded-sequenced DNA sequence is SEQ ID NO:7 and the protein sequence derived from it is listed as SEQ ID NO:8 in the Sequence Listing. The protein coding sequence begins with the ATG start codon at position 34 and ends before the stop codon at position 1149. The first 14 base pairs are attributed to the sequence of the fusion with lacZ. The polyA signal (positions 1349 to 1354) and the polyA region (positions 1366 to 1384) are found in the untranslated 3' area.

The ClGPDH132 cDNA clone with 1490 base pairs is an Eco RI-XhoI fragment, the DNA sequence of which is SEQ ID NO:5 and the amino acid sequence derived from it is shown as SEQ ID NO:6 in the Sequence Listing. The DNA fragment was sequenced double stranded. ClGPDH132 cDNA SEQ ID NO:5 is missing 14 amino acids at the N terminus in comparison with ClGPDH109 cDNA SEQ ID NO:3. The open reading frame begins at position 15 and ends at position 1115, followed by the stop codon at positions 1116 to 1118. Consequently, ClGPDH132 cDNA SEQ ID NO:5 codes for a protein with 367 amino acids SEQ ID NO:6 and likewise includes the coding area for glycerol-3-phosphate dehydrogenase with the exception of 14 amino acids. The first 14 nucleotides are to be attributed to the lac fusion sequence and the linker sequence (positions 1485 to 1490) is at the 3' end. The polyA signal and the polyA area are located at positions 1343 to 1348 and 1465 to 1484, respectively, in the untranslated 3' area.

Two classes of cDNAs can be distinguished on the basis of sequence data. Accordingly, ClGPDH20 SEQ ID NO:1 and ClGPDH30 SEQ ID NO:7 cDNAs belong to class A and ClGPDH132 SEQ ID NO:5 and ClGPDH109 SEQ ID NO:3 cDNAs belong to class B.

As FIG. 1 shows, the derived amino acid sequences of ClGPDH30 SEQ ID NO:7 and ClGPDH109 SEQ ID NO:3 cDNAs show 96% identical amino acids. At the same time, the derivative amino acid sequences of the cDNAs and those of a gene to be assigned to another class, ClGPDH30SEQ ID NO:7, were compared with the GPDH amino acid sequence of the mouse (MmGPDH SEQ ID NO:17). The differences between the amino acid sequence derived from the ClCPDH109 cDNA SEQ ID NO:3, the coded amino acid sequence of the gene and the mouse GPDH SEQ ID NO:17 in comparison with the amino acid sequence derived from ClGPDH30 SEQ ID NO:7 are shown in black. On the average, the identity of the derivative proteins of the cDNAs and the GPDH gen with the mouse protein SEQ ID NO:17 is approximately 50%.

ClGPDH20 SEQ ID NO:1 cDNA was cloned into an expression vector and expressed in *E. coli* as a fusion protein with glutathione-S-transferase. To do so, the cDNA was cloned beginning with ATG (see position 17, SEQ ID NO:1) into pGX, a derivative of the PGEXKG expression vector (K. L. Guan et al., Analytical Biochem. 192 (1991) pages 262–267). BB26-36 cells were harvested at various times after administration of IPTG isopropyl-b-thiogalactopyranoside) and their proteins were separated by gel electrophoresis. FIG. 2 shows gel electrophoretic separation of BB26-36 cell extracts. The left column shows the proteins of cells with the pGX expression vector (without fusion; 26 kDa protein) and the right side shows proteins of cells with the pGXGPDH20 expression vector which codes for a fusion protein of 67 kDa. The hourly values given indicate the times of sampling after IPTG induction. This clearly shows an enrichment of the fusion protein after two hours. An enzyme activity determination was subsequently performed by enzyme assay of GPDH with an isolated fusion protein and significant enzyme activity was measured. This finding clearly proves that ClGPDH20 SEQ ID NO:1 cDNA contains a competent gene for expression of GPDH.

Furthermore, genomic clones were isolated, where a library of genomic DNA of *Cuphea lanceolata* was screened with ClCPDH20 SEQ ID NO:1 cDNA as a probe. By this method, 31 genomic clones were isolated. The genomic clones contain a complete structure gene of a glycerol-3-phosphate dehydrogenase and alleles plus derivatives of this gene together with the promoter sequence and other regulator elements. This means that they form complete transcription units.

Figure 3:
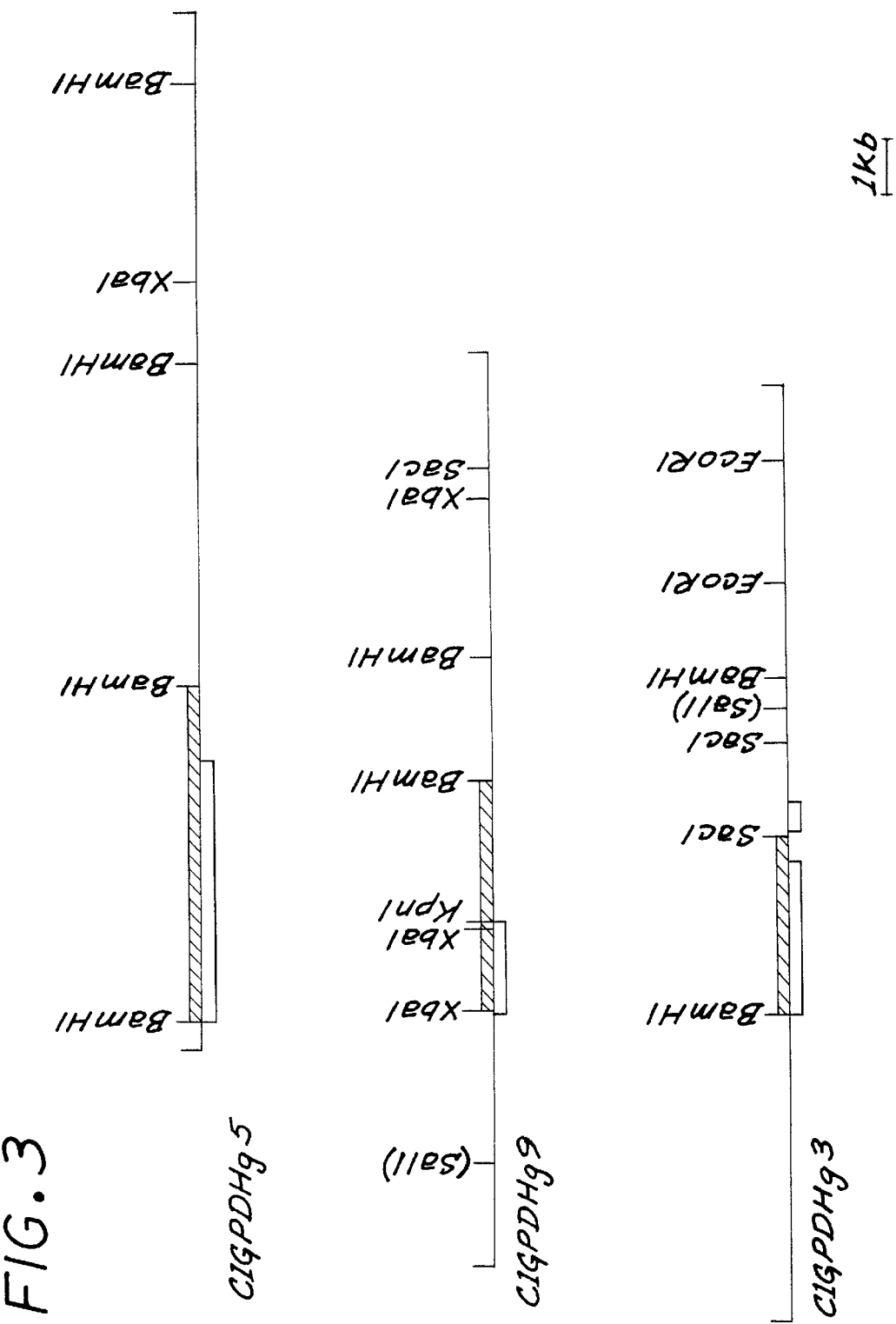
FIG. 3: Map of the insertions contained in ClGPDHg5SEQ ID NO:9, ClGPDH9 SEQ ID NO:15 and ClGPDH3 SEQ. ID NO:11 genomic clones with various restriction enzymes.

Three genomic clones are characterized below. These include the ClGPDHg3 genomic clone with a 15.9 kb DNA insertion, the ClGPDHg5 genomic clone with a 17.7 kb DNA insertion, and the ClGPDHg9 genomic clone with a 15.6 kb DNA insertion. FIG. 3 shows a map of the DNA insertions of the genomic clones with various restriction enzymes. The black bars indicate the fragments that hybridize with a 5' probe of the GPDH20 cDNA. The white bars show the areas of DNA insertions that were sequenced and are included in the Sequence Listing.

Figure 4:
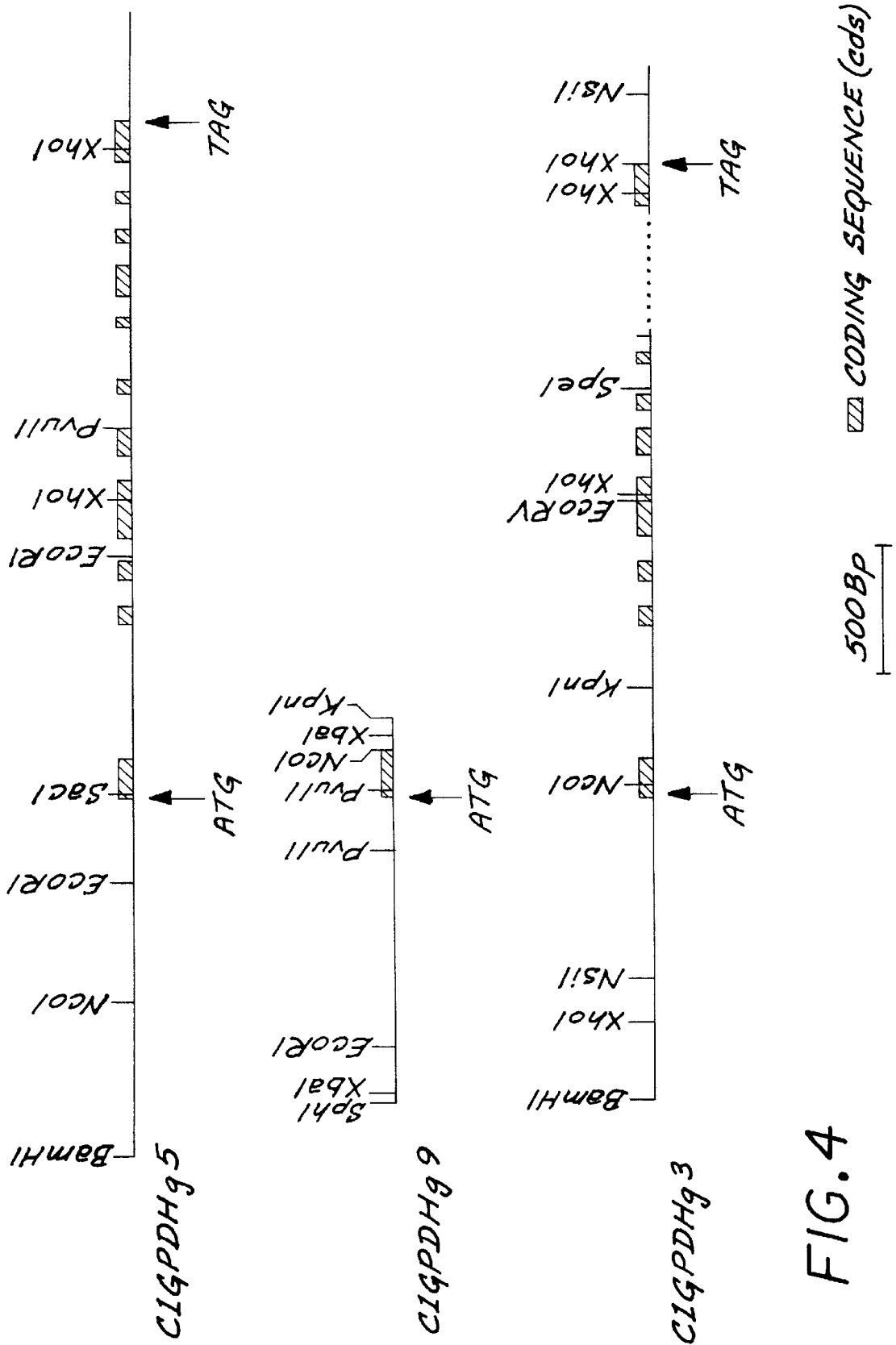
FIG. 4: Schematic diagram of the functional areas of the genes contained in the ClGPDH5SEQ ID NO:9, ClGPDH9 SEQ ID NO:15 and ClGPDH3 SEQ ID NO:11 genomic clones.

Sequence analysis of the areas presented in FIG. 3 (white bars) of the three genomic clones ClGPDHg5, ClGPDHg3 and ClGPDHg9 has shown that they contain the complete or partial structure gene of GPDH with all or most of the promoter sequence (5' direction). FIG. 4 shows a schematic diagram of the sequenced areas of the genomic clones. The ClGPDHg5, ClGPDHg9 and ClGPDHg3 genomic clones contain the complete structure genes of GPDH in addition to promoter sequences. The entire promoter of GPDH was sequenced from the ClGPDHg9 genomic clone.

Thus a 4434 bp DNA fragment of the ClGPDHg5 genomic clone contains parts of the promoter and the complete structure gene of GPDH in the 5' area. The double-stranded-sequenced DNA sequence is SEQ ID NO:9. The amino acid sequence derived from it is shown as SEQ ID NO:10 in the Sequence Listing. The protein-coding sequence interrupted by DNA areas not translated (introns) with 372 amino acids begins with the ATG start codon in position 1394 and ends before the TAG stop codon in position 4005. The putative TATA box is located at positions 1332 to 1336. Transcription presumably starts at position 1364 (Joshi, NAR 15 (1987) pages 6643–6653). The polyA signal is located in positions 4205 to 4210 at the 3' end. Position 4221 corresponds to the last nucleotide before the polyA area of ClGPDH30 SEQ ID NO:7 cDNA (see position 1365in SEQ ID NO:7).

The complete structure gene of GPDH as well as parts of the promoter in 5' direction are contained in a 4006 bp DNA fragment from the ClGPDHg3 genomic clone. The DNA sequence of the DNA fragment that was sequenced mostly as a double strand from ClGPDHg3 is SEQ ID NO:11. The amino acid sequence derived from it is shown as SEQ ID NO:12 in the Sequence Listing. The protein coding area interrupted by intron sequences begins at position 1182 (see SEQ ID NO:11) with the ATG start codon and ends with the TAG stop codon at position 190 (see SEQ ID:12. CAAT box and TATA box signal sequences are located at positions 1055 to 1058 and 1103–1107 before the start of transcription. Assumed transcription starting points are at positions 1136 and 1148. Owing to a lack of sequence data, an area of approximately 480 base pairs is not identified within the coding sequence. The polyA signal is located in the untranslated 3' area at positions 393 to 398 (SEQ ID:12).

The entire promoter as well as the first exon of the sequence coding for GPDH are contained in a 1507 bp DNA fragment from the ClGPDHg9 genomic clone. The DNA sequence that was sequenced mostly as a double strand is SEQ ID NO:15. The amino acid sequence derived from it is shown as SEQ ID NO:16 in the Sequence Listing. The TATA box is located at positions 1108 to 1112 before the start of transcription. The protein coding sequence begins with the ATG start codon at position 1193 and ends at position 1376, where an untranslated area (intron) begins. Transcription presumably starts at position 1144.

By comparing DNA sequences, it has been found that ClGPDH30 SEQ ID NO:7 cDNA, which includes a complete protein reading frame for GPDH, is identical to the GPDH gene from the ClGPDHg5 SEQ ID NO:9 genomic clone. Consequently, the ClGPDHg5 SEQ ID NO:9 genomic clone can be classified in class A (see above). The ClGPDH132 SEQ ID NO:5 cDNA with an almost complete protein reading frame for GPDH is identical to the gene from the ClGPDHg9 SEQ ID NO:15 genomic clone, which consequently may be assigned to class B (see above). The gene from the ClGPDHg3 SEQ ID NO:13 genomic clone cannot be assigned to either of the two classes, and thus forms another class C.

Genetic engineering methods (in the form of anti-sense expression or overexpression) can be used to introduce or transfer the DNA sequences according to this invention that code for a glycerol-3-phosphate dehydrogenase into plants for the production of these dehydrogenases for the purpose of altering the biosynthesis yield of these plants. Inasmuch as the DNA sequences according to this invention are not a complete transcription unit, they are preferably introduced into the plants together with suitable promoters, especially in recombinant vectors, such as binary vectors. Genomic clones can be used as separate complete transcription units for the transformation of plants in order to influence the triacyiglyceride content and the fatty acid distribution.

Any species of plants can be transformed for this purpose. Oil-bearing plants, such as rapeseed, sunflower, linseed, oil palm and soybean are preferred for this transformation in order to influence the triacyrglyceride biosynthesis in these plants in the manner desired.

The introduction of DNA sequences according to this invention that code for a glycerol-3-phosphate dehydrogenase as well as the complete genes contained in the genomic clones of a glycerol-3-phosphate dehydrogenase by the methods of genetic engineering can be performed with the aid of conventional transformation techniques. Such techniques include direct gene transfer, such as microinjection, electroporation, use of particle gun, steeping plant parts in DNA solutions, pollen or pollen tube transformation, viral vector-mediated transfer and liposome-mediated transfer as well as the transfer of appropriate recombinant Ti plasmids or Ri plasmids through *Agrobacterium tumefaciens* and transformation by plant viruses.

The DNA sequences according to this invention as well as the complete genes of a glycerol-3-phosphate dehydrogenase contained in the genomic clones are excellent for achieving a significant increase in oil production by transgeneic plants. This increase in oil yield is obtained with an increase in triacylglyceride content in the seed due to overexpression of GPDH. Furthermore, a reduction in glycerol-3-phosphate dehydrogenase can be obtained through anti-sense expression or cosuppression, so the building blocks for triacylglyceride synthesis are missing. This effect is especially beneficial when the production of wax esters (such as jojoba wax esters) in the seeds of tranisgeneic plants is to be improved. Another possible application of DNA sequences according to this invention as well as the genes from the genomic clones would be for suppressing triacylglyceride biosynthesis in transgeneic plants and making available the CoA ester as well as glycerol-3-phosphate for other biosyntheses.

Moreover, the promoters of glycerol-3-phosphate dehydrogenase genes from clones according to this invention can, for example, be used for targeted expression of chimeric genes in embryo-specific tissue. On the basis of experimental data it is assumed with regard to the specificity of the promoters that the promoters of genes from the ClGPDHg5 SEQ ID NO:9 and ClGPDHg9 SEQ ID NO:15 genomic clones are seed-specific, while the promoter of the gene from the ClGPDHg3 SEQ ID NO:11 genomic clone has little or no activity in the embryo. Thus, for example, a 1387 bp BamHI/AlwNI fragment of ClGPDHg5 SEQ ID NO:9 is suitable for transcriptional fusion, a 1189 base pair SphI/NarI fragment of ClGPDHg9 SEQ ID NO:15 is suitable for translational fusion and a 1172 base pair BamHI/BsmAI (part.) fragment of ClGPDHg3 SEQ ID NO:11 is suitable for transcriptional fusion. Larger (or smaller) promoter fragments can be used for expression of chimeric genes on the basis of additional clones present on the genetic clones. Likewise, any regulatory sequences located downstream from the first codon of the GPDH gene are obtained for targeted expression of chimeric genes from the cloned fragments of genomic DNA.

Figure 5:
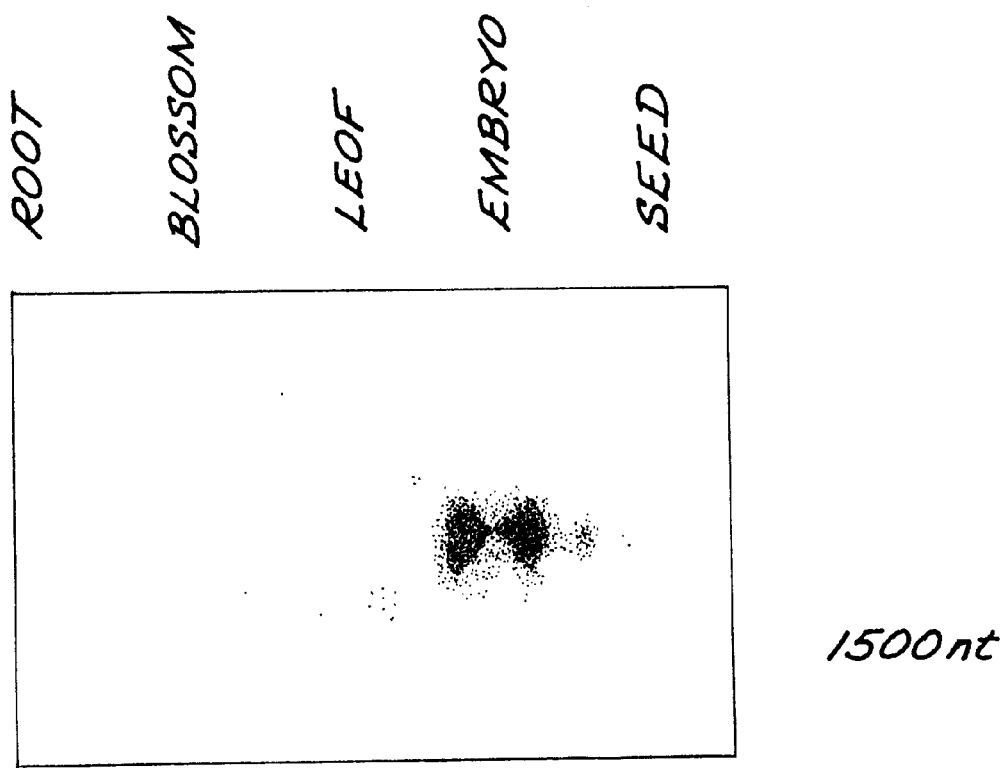
FIG. 5: Northern Blot with RNAs from various plant tissues, hybridized with ClGPDH20 SEQ ID NO:1 cDNA as a probe.

Northern Blot analysis with polyA$^+$-RNA from various *Cuphea lanceolata* tissues with ClGPDH20 SEQ ID NO:1 cDNA as a probe shows very large amounts of RNA in embryos in comparison with other tissues (see FIG. 5). The increase in RNA correlates with increased gene expression and consequently indicates an extremely strong promoter.

The following examples are presented to illustrate this invention.

EXAMPLES

The plant material used in the context of the present invention was obtained from *Cuphea lanceolata* (Lythraceae) (small lanceolate tube flower).

Example 1

Production of Glycerol-3-phosphate Dehydroaenase cDNAs from *Cuphea Lanceolata*

A cDNA library was prepared from *Cuphea lanceolata* (wild type) took place with the help of the ZAP® cDNA synthesis kit according to the manufacturer's instructions (Stratagene, La Jolla, USA). Messenger RNA from isolated immature embryos about two to three weeks old was used as raw material for the synthesis of the cDNAs. The cDNA library obtained in this way contained $9.5 \times 10^5$ recombinant phages.

Functional complementation for isolation of cDNAs that code for a glycerol-3-phosphate dehydrogenase was performed with the *E. Coli BB*26-36 strain (R. M. Bell, J. Bact. 117 (1974) pages 1065–1076). The bacterial medium for culturing BB26-36 (bearing the plsB26 and plsX mutations) was supplemented with 0.1% glycerol to supplement the bacteria. A medium without glycerol was used for functional complementation.

The pBluescript plasmids were cut out of the above cDNA library in 1-ZAP II according to the manufacturer's instructions (Stratagene) by in vivo excision using helper phages and then packed in phage coats: 200 ml of XL1Blue *E. Coli* cells ($OD_{600}$=1) were infected with $5 \times 10^5$ pfu of the 1-ZAP II cDNA library, and, in order to guarantee coinfection, were also infected with a tenfold amount of f1 R408 helper phages. After incubating for 15 minutes at a temperature of 37° C. for phage adsorption, 5 ml 2×YT medium were added and agitated for three hours more at a temperature of 37° C. During this time, the cells of the pBluescript plasmids packed in the coats of helper phages are secreting the so-called phagemids into the medium. The bacteria were killed and the 1 phages were inactivated by a heating for 20 minutes at 70° C. After centrifuging, the supernatant containing helper phages along with phagemids was removed. This supernatant was used for infection of the mutant BB26-36 strain.

Complementation was performed after infecting the *E. coli* BB26-36 strain with phagemids containing cDNA plasmids that code for a glycerol-3-phosphate dehydrogenase. M56-LP medium (Bell, loc. cit.) with 50 mg ampicillin was used for selection (without glycerol-3-phosphate). Retransformation of BB26-36 was performed by the method of D. Hanahan, J. Mol. Biol. 166 (1983) pages 557–580, with subsequent plating on the selective medium mentioned.

Delection clones for determining the sequence of the DNA fragments of positive cDNA clones were produced by means of exonuclease III (Strategene) and were sequenced according to the method of Sanger et al., Proc. Nat. Acad. Sci. 74 (1977) pages 5463–5467. Some of the DNA sequencing was performed radioactively with the help of the $T^7$ Sequencing® Kit or with a Pharmacia Automated Laser Fluorescent A.L.F.® DNA sequencer. The sequences were analyzed with the help of computer software from the University of Wisconsin Genetics Computer Group (J. Devereux et al., Nucl. Acids Res. 12 (1984) pages 387–394).

Furthermore, cDNA clones were isolated by screening a cDNA library from *Cuphea lanceolata* with ClGPDH20 SEQ ID NO:1 cDNA as a probe. For this, a cDNA library from *Cuphea lanceolata* (wild type) was produced according to the manufacturer's instructions with the ZAP® cDNA Synthesis Kit. Messenger RNA from isolated, immature embryos about two to three weeks old was the raw material for synthesis of the cDNAs. The cDNA library obtained contained $9.6 \times 10^5$ recombinant phages with approx. 50% clones with more than 500 bp insertions. The cDNA library was examined with CLGPDH20 SEQ ID NO:1 as a probe, and 18 cDNAs were isolated and partially or completely sequenced in the usual manner. Of these cDNAs, 12 were class A, and 6 cDNAs were in class B.

The enzyme measurements were performed with the fusion protein according to the method of Santora et al., Arch. Biochem. Biophys. 196 (1979) pages 403–411.

Example 2

Production of Genomic Clones of Glycerol-3-phosphate Dehydrogenase from *Cuphea lanceolata*

Genomic DNA from young *Cuphea lanceolata* leaves were isolated for this example (S. L. Della Porta et al.,

*Plant. Mol. Biol. Rep.* 1, (1983) pages 19–21). The DNA was then partially cleaved with the restriction enzyme Sau3A, whereupon DNA fragments of 11,000 to 19,000 base pairs were cloned in vector 1FIXII (Stratagene) that was cleaved with XhoI after the respective interfaces were partially filled with two nucleotides in any given case. The genomic DNA library that was not reproduced amounted to 5.4 times the genome of *Cuphea lanceolata*. Thirty-one genomic clones were then isolated from this library with ClGPDH20-cDNA as a probe.

The three genomic clones ClGPDHg3 (15.9 kb DNA insertion), ClGPDHg5 (17.7 kb DNA insertion) and ClGPDHg9 (15.6 kb DNA insertion) were characterized in greater detail. Suitable subclones were produced in the usual manner and their insertions were sequenced with the ExoIII/Mung bean kit and also with oligonucleotide primers in order to bridge any gaps.

If any of the procedures customary in molecular biology have not have been described adequately here, such procedures were performed by standard methods as described in Sambrook et al., A Laboratory Manual, second edition (1989).

What is claimed is:

1. A DNA molecule which is isolated from a plant and codes for glycerol-3-phosphate dehydrogenase.

2. The DNA molecule according to claim 1, wherein said DNA molecule is isolated from *Cuphea lanceolata*.

3. The DNA molecule according to claim 1, obtained by functional complementation of mutants of a microorganism.

4. The DNA molecule according to claim 3, wherein the microorganism is *E. coli*.

5. A genomic clone which comprises a complete gene encoding glycerol-3-phosphate dehydrogenase isolated from *Cuphea lanceolata*.

6. The genomic clone according to claim 5, wherein the complete gene comprises the promoter sequence and other regulatory elements in addition to the structural gene.

7. An isolated promoter region of the gene encoding glycerol-3-phosphate dehydrogenase from the genomic clone according to claim 5.

8. An isolated promoter region of a gene encoding glycerol-3-phosphate dehydrogenase from a genomic clone that is selected from the group consisting of ClGPDHg5, ClGPDHg3 and ClGPDHg9.

* * * * *

UNITED STATES PATENT AND TRADEMARK OFFICE
CERTIFICATE OF CORRECTION

PATENT NO. : 6,103,520
DATED : August 15, 2000
INVENTOR(S) : Töpfer et al.

It is certified that error appears in the above-identified patent and that said Letters Patent is hereby corrected as shown below:

Column 2, line 56, "ClGPDH3" should be --ClGPDHg3--.

Column 8, line 13, "1-ZAP" should be -- $\lambda$ ZAP--.

Column 8, line 21, "1 phages" should be -- $\lambda$ phages--.

Signed and Sealed this

Twenty-fourth Day of April, 2001

Attest:

Attesting Officer

NICHOLAS P. GODICI

Acting Director of the United States Patent and Trademark Office

UNITED STATES PATENT AND TRADEMARK OFFICE
CERTIFICATE OF CORRECTION

PATENT NO. : 6,103,520
DATED : August 15, 2000
INVENTOR(S) : Töpfer et al.

Page 1 of 1

It is certified that error appears in the above-identified patent and that said Letters Patent is hereby corrected as shown below:

Column 2,
Lines 51 and 55, "ClGPDH9" should be -- ClGPDHg9 --.
Line 52, "ClGPDH3" should be -- ClGPDHg3 --.
Line 55, "ClGPDH5" should be -- ClGPDHg5 --.

Column 5,
Line 19, "ClCPDH20" should be -- ClGPDH20 --.
Line 30, after "insertion.", insert -- A viable culture of ClGPDHg3 was deposited pursuant to the terms of the Budapest Treaty in the DSMZ-DEUTSCHE SAMMLUNG VON MIKROORGANISMEN UND ZELLKULTUREN GmbH, having the address of Mascheroder Weg 1b, D-38124 Braunschweig, Federal Republic of Germany, on March 15, 2000, with the accession number DSM 13369. A viable culture of ClGPDHg5 was deposited pursuant to the terms of the Budapest Treaty in the DSMZ-DEUTSCHE SAMMLUNG VON MIKROORGANISMEN UND ZELLKULTUREN GmbH, having the address of Mascheroder Weg, 1b,D-38124 Braunschweig, Federal Republic of Germany, on March 15, 2000, with the accession number 13370. A viable culture of ClGPDHg9 was deposited pursuant to the terms of the Budapest Treaty in the DSMZ-DEUTSCHE SAMMLUNG VON MIKROORGANISMEN UND ZELLKULTUREN GmbH, having the address of Mascheroder Weg 1b, D-38124 Braunschweig, Federal Republic of Germany, on March 15, 2000, with the accession number DSM 13371. --.

Column 8,
Line 66, "*leaves were isolated for ... Biol Rep.*"

Column 54,
Line 24, after "ClGPDHg5", insert -- (Accession number DSM 13370) --.
Line 25, after "ClGPDHg3", insert -- (Accession number DSM 13369) --.
Line 25, after "ClGPDHg9", insert -- (Accession number DSM 13371) --.

Signed and Sealed this

Twenty-seventh Day of November, 2001

Attest:

*Attesting Officer*

NICHOLAS P. GODICI
*Acting Director of the United States Patent and Trademark Office*

SEQUENCE LISTING (1) GENERAL INFORMATION:

(iii) NUMBER OF SEQUENCES: 17

(2) INFORMATION FOR SEQ ID NO:1:

(i) SEQUENCE CHARACTERISTICS:
      (A) LENGTH: 1354 base pairs
      (B) TYPE: nucleic acid
      (C) STRANDEDNESS: double
      (D) TOPOLOGY: linear (ii) MOLECULE TYPE: cDNA to mRNA (iii) HYPOTHETICAL: NO (iv) ANTI-SENSE: NO (vi) ORIGINAL SOURCE:
      (A) ORGANISM: Cuphea lanceolata (vii) IMMEDIATE SOURCE:
      (A) LIBRARY: ZAP cDNA library
      (B) CLONE: C1GPDH20

(ix) FEATURE:
      (A) NAME/KEY: CDS
      (B) LOCATION: 17..1132

(xi) SEQUENCE DESCRIPTION: SEQ ID NO:1:

```
GAATTCGGCA CGAGCA ATG GCT CCC TCT GAG CTC AAC TGC ACC CAC CAG                49
               Met Ala Pro Ser Glu Leu Asn Cys Thr His Gln
                 1               5                  10

AAC CAG CAT TCA AGC GGT TAC GAC GGA CCC AGA TCG AGG GTC ACC GTT              97
Asn Gln His Ser Ser Gly Tyr Asp Gly Pro Arg Ser Arg Val Thr Val
             15                  20                  25

GTC GGT AGT GGA AAC TGG GGT AGT GTT GCT GCC AAG CTC ATT GCT ACC             145
Val Gly Ser Gly Asn Trp Gly Ser Val Ala Ala Lys Leu Ile Ala Thr
         30                  35                  40

AAT ACC CTC AAG CTT CCA TCT TTT CAT GAT GAA GTG AGA ATG TGG GTA             193
Asn Thr Leu Lys Leu Pro Ser Phe His Asp Glu Val Arg Met Trp Val
     45                  50                  55

TTT GAG GAG ACG CTA CCG AGC GGC GAG AAG CTT ACT GAT GTC ATC AAC             241
Phe Glu Glu Thr Leu Pro Ser Gly Glu Lys Leu Thr Asp Val Ile Asn
 60                  65                  70                  75

CAG ACC AAT GAA AAT GTT AAG TAT CTC CCC GGA ATT AAG CTC GGT AGG             289
Gln Thr Asn Glu Asn Val Lys Tyr Leu Pro Gly Ile Lys Leu Gly Arg
                 80                  85                  90

AAT GTT GTT GCA GAT CCA GAC CTC GAA AAC GCA GTT AAG GAT GCA AAT             337
Asn Val Val Ala Asp Pro Asp Leu Glu Asn Ala Val Lys Asp Ala Asn
             95                 100                 105
```

```
ATG CTC GTG TTT GTG ACA CCG CAT CAG TTC ATG GAG GGC ATC TGC AAA      385
Met Leu Val Phe Val Thr Pro His Gln Phe Met Glu Gly Ile Cys Lys
        110                 115                 120

AGA CTC GAA GGG AAA ATA CAA GAA GGA GCA CAG GCT CTC TCC CTT ATA      433
Arg Leu Glu Gly Lys Ile Gln Glu Gly Ala Gln Ala Leu Ser Leu Ile
125                 130                 135

AAG GGC ATG GAG GTC AAA ATG GAG GGG CCT TGC ATG ATC TCG AGC TTA      481
Lys Gly Met Glu Val Lys Met Glu Gly Pro Cys Met Ile Ser Ser Leu
140                 145                 150                 155

ATC TCT GAT CTT CTC GGG ATT AAC TGC TGT GTC CTA ATG GGG GCA AAC      529
Ile Ser Asp Leu Leu Gly Ile Asn Cys Cys Val Leu Met Gly Ala Asn
                160                 165                 170

ATC GCT AAT GAG ATT GCT GTT GAG AAA TTC AGT GAA GCG ACA GTC GGG      577
Ile Ala Asn Glu Ile Ala Val Glu Lys Phe Ser Glu Ala Thr Val Gly
            175                 180                 185

TTC AGA GAA AAT AGA GAT ATT GCA GAG AAA TGG GTT CAG CTC TTT AGC      625
Phe Arg Glu Asn Arg Asp Ile Ala Glu Lys Trp Val Gln Leu Phe Ser
        190                 195                 200

ACT CCG TAC TTC ATG GTC TCA GCT GTT GAA GAT GTT GAA GGA GTA GAA      673
Thr Pro Tyr Phe Met Val Ser Ala Val Glu Asp Val Glu Gly Val Glu
    205                 210                 215

CTT TGT GGA ACA CTG AAG AAT ATC GTG GCC ATA GCA GCC GGT TTT GTG      721
Leu Cys Gly Thr Leu Lys Asn Ile Val Ala Ile Ala Ala Gly Phe Val
220                 225                 230                 235

GAT GGA TTG GAG ATG GGA AAC AAC ACA AAA GCA GCA ATT ATG AGG ATC      769
Asp Gly Leu Glu Met Gly Asn Asn Thr Lys Ala Ala Ile Met Arg Ile
                240                 245                 250

GGG TTA CGG GAG ATG AAG GCA TTC TCC AAG CTT TTG TTT CCA TCT GTT      817
Gly Leu Arg Glu Met Lys Ala Phe Ser Lys Leu Leu Phe Pro Ser Val
            255                 260                 265

AAG GAC ACT ACT TTC TTC GAG AGC TGT GGA GTC GCT GAC CTC ATC ACA      865
Lys Asp Thr Thr Phe Phe Glu Ser Cys Gly Val Ala Asp Leu Ile Thr
        270                 275                 280

ACT TGT TTG GGC GGG AGA AAC AGA AAA GTT GCT GAG GCT TTT GCA AAG      913
Thr Cys Leu Gly Gly Arg Asn Arg Lys Val Ala Glu Ala Phe Ala Lys
    285                 290                 295

AAT GGC GGG AAA AGG TCA TTC GAT GAT CTC GAA GCA GAG ATG CTC CGG      961
Asn Gly Gly Lys Arg Ser Phe Asp Asp Leu Glu Ala Glu Met Leu Arg
300                 305                 310                 315

GGG CAA AAA TTA CAG GGT GTC TCA ACA GCA AAG GAG GTC TAT GAA GTC     1009
Gly Gln Lys Leu Gln Gly Val Ser Thr Ala Lys Glu Val Tyr Glu Val
                320                 325                 330

TTG GGG CAC CGA GGC TGG CTC GAG CTG TTC CCG CTC TTC TCA ACC GTG     1057
Leu Gly His Arg Gly Trp Leu Glu Leu Phe Pro Leu Phe Ser Thr Val
            335                 340                 345

CAC GAG ATA TCC ACT GGC CGT CTG CCT CCT TCA GCC ATC GTC GAA TAC     1105
His Glu Ile Ser Thr Gly Arg Leu Pro Pro Ser Ala Ile Val Glu Tyr
        350                 355                 360

AGC GAA CAA AAA ACC ATC TTC TCT TGG TAGAGCAAGA GGCTGCCCTT           1152
Ser Glu Gln Lys Thr Ile Phe Ser Trp
    365                 370

GAAAGACTAA GAGCCACCCT GCCCTGTTTA AAGGGCTAAA AGTTTAATAT TTCTCTGCAG   1212

CCTAAACAGT CGGAAACATT GAAAATCTAG GATGTATAAG AAAAAAAAAA GAAGGTTTGA   1272

AGGAAGTATG GATGGGCATG AATGTATTTA TTTTCGGTAT ACTCTTTTTC TGCAAAAATA   1332

ATTTCTTCAG AAAGGGGGGC CC                                           1354
```

(2) INFORMATION FOR SEQ ID NO:2:

(i) SEQUENCE CHARACTERISTICS:
    (A) LENGTH: 372 amino acids
    (B) TYPE: amino acid
    (D) TOPOLOGY: linear (ii) MOLECULE TYPE: protein (xi) SEQUENCE DESCRIPTION: SEQ ID NO:2:

```
Met Ala Pro Ser Glu Leu Asn Cys Thr His Gln Asn Gln His Ser Ser
 1               5                  10                  15

Gly Tyr Asp Gly Pro Arg Ser Arg Val Thr Val Gly Ser Gly Asn
                20                  25                  30

Trp Gly Ser Val Ala Ala Lys Leu Ile Ala Thr Asn Thr Leu Lys Leu
                35                  40                  45

Pro Ser Phe His Asp Glu Val Arg Met Trp Val Phe Glu Glu Thr Leu
     50                  55                  60

Pro Ser Gly Glu Lys Leu Thr Asp Val Ile Asn Gln Thr Asn Glu Asn
 65                  70                  75                  80

Val Lys Tyr Leu Pro Gly Ile Lys Leu Gly Arg Asn Val Val Ala Asp
                85                  90                  95

Pro Asp Leu Glu Asn Ala Val Lys Asp Ala Asn Met Leu Val Phe Val
                100                 105                 110

Thr Pro His Gln Phe Met Glu Gly Ile Cys Lys Arg Leu Glu Gly Lys
                115                 120                 125

Ile Gln Glu Gly Ala Gln Ala Leu Ser Leu Ile Lys Gly Met Glu Val
                130                 135                 140

Lys Met Glu Gly Pro Cys Met Ile Ser Ser Leu Ile Ser Asp Leu Leu
145                 150                 155                 160

Gly Ile Asn Cys Cys Val Leu Met Gly Ala Asn Ile Ala Asn Glu Ile
                165                 170                 175

Ala Val Glu Lys Phe Ser Glu Ala Thr Val Gly Phe Arg Glu Asn Arg
                180                 185                 190

Asp Ile Ala Glu Lys Trp Val Gln Leu Phe Ser Thr Pro Tyr Phe Met
                195                 200                 205

Val Ser Ala Val Glu Asp Val Glu Gly Val Glu Leu Cys Gly Thr Leu
                210                 215                 220

Lys Asn Ile Val Ala Ile Ala Gly Phe Val Asp Gly Leu Glu Met
225                 230                 235                 240

Gly Asn Asn Thr Lys Ala Ala Ile Met Arg Ile Gly Leu Arg Glu Met
                245                 250                 255

Lys Ala Phe Ser Lys Leu Leu Phe Pro Ser Val Lys Asp Thr Thr Phe
                260                 265                 270

Phe Glu Ser Cys Gly Val Ala Asp Leu Ile Thr Thr Cys Leu Gly Gly
                275                 280                 285

Arg Asn Arg Lys Val Ala Glu Ala Phe Ala Lys Asn Gly Gly Lys Arg
                290                 295                 300

Ser Phe Asp Asp Leu Glu Ala Glu Met Leu Arg Gly Gln Lys Leu Gln
305                 310                 315                 320

Gly Val Ser Thr Ala Lys Glu Val Tyr Glu Val Leu Gly His Arg Gly
                325                 330                 335

Trp Leu Glu Leu Phe Pro Leu Phe Ser Thr Val His Glu Ile Ser Thr
                340                 345                 350

Gly Arg Leu Pro Pro Ser Ala Ile Val Glu Tyr Ser Glu Gln Lys Thr
                355                 360                 365

Ile Phe Ser Trp
```

(2) INFORMATION FOR SEQ ID NO:3:

(i) SEQUENCE CHARACTERISTICS:
        (A) LENGTH: 1464 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (A) ORGANISM: Cuphea lanceolata (vii) IMMEDIATE SOURCE:
        (A) LIBRARY: ZAP cDNA library
        (B) CLONE: C1GPDH109

(ix) FEATURE:
        (A) NAME/KEY: CDS
        (B) LOCATION: 45..1187

(xi) SEQUENCE DESCRIPTION: SEQ ID NO:3:

```
GAATTCGGCA CGAGCTTCCT CTGTTCTTCC TCTCTGCCTC TGCA ATG GCG CCT GCC      56
                                                  Met Ala Pro Ala
                                                   1

TTC GAA CCC CAT CAG CTG GCT CCC TCT GAG CTT AAC TCT GCC CAC CAG      104
Phe Glu Pro His Gln Leu Ala Pro Ser Glu Leu Asn Ser Ala His Gln
 5                  10                  15                  20

AAC CCA CAT TCA GGC GGA TAT GAC GGA CCC AGA TCG AGG GTC ACT GTC      152
Asn Pro His Ser Gly Gly Tyr Asp Gly Pro Arg Ser Arg Val Thr Val
                25                  30                  35

GTC GGC AGC GGA AAC TGG GGC AGC GTC GCT GCC AAG CTC ATT GCT TCC      200
Val Gly Ser Gly Asn Trp Gly Ser Val Ala Ala Lys Leu Ile Ala Ser
            40                  45                  50

AAC ACC CTC AAG CTC CCA TCT TTC CAT GAT GAA GTG AGG ATG TGG GTA      248
Asn Thr Leu Lys Leu Pro Ser Phe His Asp Glu Val Arg Met Trp Val
        55                  60                  65

TTT GAG GAG ACT CTA CCG GGC GGC GAG AAG CTC ACT GAT ATC ATC AAC      296
Phe Glu Glu Thr Leu Pro Gly Gly Glu Lys Leu Thr Asp Ile Ile Asn
 70                  75                  80

CAG ACC AAT GAA AAT GTT AAA TAT CTT CCC GGA ATT AAG CTC GGT GGG      344
Gln Thr Asn Glu Asn Val Lys Tyr Leu Pro Gly Ile Lys Leu Gly Gly
 85                  90                  95                 100

AAT GTT GTT GCT GAT CCA GAC CTC GAA AAT GCA GTT AAG GAT GCA AAT      392
Asn Val Val Ala Asp Pro Asp Leu Glu Asn Ala Val Lys Asp Ala Asn
                105                 110                 115

ATG CTC GTG TTT GTC ACA CCG CAT CAG TTC ATG GAG GGC ATC TGC AAA      440
Met Leu Val Phe Val Thr Pro His Gln Phe Met Glu Gly Ile Cys Lys
            120                 125                 130

AGA CTT GTC GGG AAG ATA CAG GAA GGA GCG CAG GCT CTC TCC CTT ATA      488
Arg Leu Val Gly Lys Ile Gln Glu Gly Ala Gln Ala Leu Ser Leu Ile
        135                 140                 145

AAA GGC ATG GAG GTC AAG ATG GAG GGG CCT TGC ATG ATC TCG AGC CTA      536
Lys Gly Met Glu Val Lys Met Glu Gly Pro Cys Met Ile Ser Ser Leu
150                 155                 160

ATC TCA GAT CTT CTC GGG ATC AAC TGC TGT GTC CTT AAT GGG GCA AAC      584
Ile Ser Asp Leu Leu Gly Ile Asn Cys Cys Val Leu Asn Gly Ala Asn
165                 170                 175                 180

ATC GCT AAT GAG ATT GCT GTT GAG AAA TTC AGT GAA GCG ACT GTC GGG      632
```

```
Ile Ala Asn Glu Ile Ala Val Glu Lys Phe Ser Glu Ala Thr Val Gly
                185                 190                 195

TTC AGA GAA AAT AGA GAT ATT GCG GAA AAA TGG GTT CAG CTC TTT AGC      680
Phe Arg Glu Asn Arg Asp Ile Ala Glu Lys Trp Val Gln Leu Phe Ser
                200                 205                 210

ACT CCA TAC TTC ATG GTC TCA GCT GTT GAA GAT GTT GAA GGA GTA GAG      728
Thr Pro Tyr Phe Met Val Ser Ala Val Glu Asp Val Glu Gly Val Glu
                215                 220                 225

CTT TGT GGA ACA CTG AAG AAT ATT GTG GCC ATA GCA GCG GGT TTT GTT      776
Leu Cys Gly Thr Leu Lys Asn Ile Val Ala Ile Ala Ala Gly Phe Val
        230                 235                 240

GAT GGA TTG GAG ATG GGA AAC AAC ACA AAA GCG GCA ATT ATG AGG ATC      824
Asp Gly Leu Glu Met Gly Asn Asn Thr Lys Ala Ala Ile Met Arg Ile
245                 250                 255                 260

GGG CTG CGG GAG ATG AAA GCG TTC TCC AAG CTT TTG TTT CCA TCT GTT      872
Gly Leu Arg Glu Met Lys Ala Phe Ser Lys Leu Leu Phe Pro Ser Val
                265                 270                 275

AAG GAC ACT ACT TTT TTC GAG AGC TGC GGA GTC GCT GAT CTC ATC ACA      920
Lys Asp Thr Thr Phe Phe Glu Ser Cys Gly Val Ala Asp Leu Ile Thr
                280                 285                 290

ACT TGT TTG GGC GGA AGA AAC AGA AAA GTC GCT GAG GCT TTT GCA AAG      968
Thr Cys Leu Gly Gly Arg Asn Arg Lys Val Ala Glu Ala Phe Ala Lys
            295                 300                 305

AAT GGC GGA AAC AGG TCA TTT GAT GAT CTC GAA GCA GAG ATG CTC CGG     1016
Asn Gly Gly Asn Arg Ser Phe Asp Asp Leu Glu Ala Glu Met Leu Arg
310                 315                 320

GGG CAA AAA TTA CAG GGT GTC TCG ACA GCG AAA GAG GTC TAC GAG GTC     1064
Gly Gln Lys Leu Gln Gly Val Ser Thr Ala Lys Glu Val Tyr Glu Val
325                 330                 335                 340

CTG AGG CAC CGA GGC TGG CTC GAG TTG TTC CCG CTC TTC TCA ACC GTG     1112
Leu Arg His Arg Gly Trp Leu Glu Leu Phe Pro Leu Phe Ser Thr Val
                345                 350                 355

CAT GAG ATC TCC AGT GGC CGT CTG CCT CCT TCA GCC ATT GTT GAA TAC     1160
His Glu Ile Ser Ser Gly Arg Leu Pro Pro Ser Ala Ile Val Glu Tyr
                360                 365                 370

AGC GAA CAA AAG CCT ACC TTC TCT TGG TAGAGAAAGA AACCAGGAAG           1207
Ser Glu Gln Lys Pro Thr Phe Ser Trp
                375                 380

AACGGCGAGC CACTGTCCCC CGTTTAAAGG TTTACTATTT CTCTCTGCAC TTTGCAGCCT   1267

GAAGAGTCGG AAACATAGAA AATCTAGGAA GTTTCAGAAA AAGGAAGGTT TGGAGGATGT   1327

ATGGATGATA TATATACTAG GTGGGTATGA AGAGGAAGTT ATTACTATGA TGTTGGTATG   1387

TGGTAATGGC TAAGTACATG AGATCAAATA AATAGACAGA CCTTGGTTTC TTCTTTCTAA   1447

AAAAAAAGGG GGGGCCC                                                 1464

(2) INFORMATION FOR SEQ ID NO:4:

(i) SEQUENCE CHARACTERISTICS:
        (A) LENGTH: 381 amino acids
        (B) TYPE: amino acid
        (D) TOPOLOGY: linear (ii) MOLECULE TYPE: protein (xi) SEQUENCE DESCRIPTION: SEQ ID NO:4:

Met Ala Pro Ala Phe Glu Pro His Gln Leu Ala Pro Ser Glu Leu Asn
 1               5                  10                  15

Ser Ala His Gln Asn Pro His Ser Gly Gly Tyr Asp Gly Pro Arg Ser
                20                  25                  30
```

```
Arg Val Thr Val Val Gly Ser Gly Asn Trp Gly Ser Val Ala Ala Lys
             35                  40                  45

Leu Ile Ala Ser Asn Thr Leu Lys Leu Pro Ser Phe His Asp Glu Val
 50                  55                  60

Arg Met Trp Val Phe Glu Thr Leu Pro Gly Gly Glu Lys Leu Thr
 65              70                  75                      80

Asp Ile Ile Asn Gln Thr Asn Glu Asn Val Lys Tyr Leu Pro Gly Ile
                 85                  90                  95

Lys Leu Gly Gly Asn Val Val Ala Asp Pro Asp Leu Glu Asn Ala Val
                100                 105                 110

Lys Asp Ala Asn Met Leu Val Phe Val Thr Pro His Gln Phe Met Glu
                115                 120                 125

Gly Ile Cys Lys Arg Leu Val Gly Lys Ile Gln Glu Gly Ala Gln Ala
            130                 135                 140

Leu Ser Leu Ile Lys Gly Met Glu Val Lys Met Glu Gly Pro Cys Met
145                 150                 155                 160

Ile Ser Ser Leu Ile Ser Asp Leu Leu Gly Ile Asn Cys Cys Val Leu
                165                 170                 175

Asn Gly Ala Asn Ile Ala Asn Glu Ile Ala Val Glu Lys Phe Ser Glu
                180                 185                 190

Ala Thr Val Gly Phe Arg Glu Asn Arg Asp Ile Ala Glu Lys Trp Val
            195                 200                 205

Gln Leu Phe Ser Thr Pro Tyr Phe Met Val Ser Ala Val Glu Asp Val
210                 215                 220

Glu Gly Val Glu Leu Cys Gly Thr Leu Lys Asn Ile Val Ala Ile Ala
225                 230                 235                 240

Ala Gly Phe Val Asp Gly Leu Glu Met Gly Asn Asn Thr Lys Ala Ala
                245                 250                 255

Ile Met Arg Ile Gly Leu Arg Glu Met Lys Ala Phe Ser Lys Leu Leu
            260                 265                 270

Phe Pro Ser Val Lys Asp Thr Thr Phe Phe Glu Ser Cys Gly Val Ala
            275                 280                 285

Asp Leu Ile Thr Thr Cys Leu Gly Gly Arg Asn Arg Lys Val Ala Glu
            290                 295                 300

Ala Phe Ala Lys Asn Gly Gly Asn Arg Ser Phe Asp Asp Leu Glu Ala
305                 310                 315                 320

Glu Met Leu Arg Gly Gln Lys Leu Gln Gly Val Ser Thr Ala Lys Glu
                325                 330                 335

Val Tyr Glu Val Leu Arg His Arg Gly Trp Leu Glu Leu Phe Pro Leu
                340                 345                 350

Phe Ser Thr Val His Glu Ile Ser Ser Gly Arg Leu Pro Pro Ser Ala
            355                 360                 365

Ile Val Glu Tyr Ser Glu Gln Lys Pro Thr Phe Ser Trp
370                 375                 380
```

(2) INFORMATION FOR SEQ ID NO:5:

(i) SEQUENCE CHARACTERISTICS:
        (A) LENGTH: 1490 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO -continued

```
    (iv) ANTI-SENSE: NO (vi) ORIGINAL SOURCE:
         (A) ORGANISM: Cuphea lanceolata (vii) IMMEDIATE SOURCE:
         (A) LIBRARY: ZAP cDNA library
         (B) CLONE: C1GPDH132

(ix) FEATURE:
         (A) NAME/KEY: CDS
         (B) LOCATION: 15..1115

(xi) SEQUENCE DESCRIPTION: SEQ ID NO:5:
```

| | | | | | | | | | | | | |
|---|---|---|---|---|---|---|---|---|---|---|---|---|
| GAATTCGGCA CGAG | CTT | AAC | TCT | GCC | CAC | CAG | AAC | CCA | CAT | TCC | AGC | GGA | 50 |
| | Leu | Asn | Ser | Ala | His | Gln | Asn | Pro | His | Ser | Ser | Gly | |
| | 1 | | | 5 | | | | | 10 | | | | |
| TAT | GAA | GGA | CCC | AGA | TCG | AGG | GTC | ACC | GTC | GTT | GGC | AGC | GGC | AAC | TGG | 98 |
| Tyr | Glu | Gly | Pro | Arg | Ser | Arg | Val | Thr | Val | Val | Gly | Ser | Gly | Asn | Trp | |
| | 15 | | | | 20 | | | | | 25 | | | | | | |
| GGC | AGC | GTC | GCT | GCC | AAG | CTC | ATT | GCT | TCC | AAC | ACC | CTC | AAG | CTC | CCA | 146 |
| Gly | Ser | Val | Ala | Ala | Lys | Leu | Ile | Ala | Ser | Asn | Thr | Leu | Lys | Leu | Pro | |
| 30 | | | | | 35 | | | | | 40 | | | | | | |
| TCT | TTC | CAT | GAT | GAA | GTG | AGG | ATG | TGG | GTA | TTT | GAG | GAG | ACT | CTA | CCG | 194 |
| Ser | Phe | His | Asp | Glu | Val | Arg | Met | Trp | Val | Phe | Glu | Glu | Thr | Leu | Pro | |
| 45 | | | | | 50 | | | | | 55 | | | | | 60 | |
| GGC | GGC | GAG | AAG | CTC | ACT | GAT | ATC | ATC | AAC | CAG | ACC | AAT | GAA | AAT | GTT | 242 |
| Gly | Gly | Glu | Lys | Leu | Thr | Asp | Ile | Ile | Asn | Gln | Thr | Asn | Glu | Asn | Val | |
| | | | | 65 | | | | | 70 | | | | | 75 | | |
| AAA | TAT | CTT | CCC | GGA | ATT | AAG | CTC | GGT | AGG | AAT | GTT | GTT | GCA | GAT | CCA | 290 |
| Lys | Tyr | Leu | Pro | Gly | Ile | Lys | Leu | Gly | Arg | Asn | Val | Val | Ala | Asp | Pro | |
| | | | 80 | | | | | 85 | | | | | 90 | | | |
| GAC | CTC | GAA | AAC | GCA | GTT | AAG | GAT | GCA | AAT | ATG | CTC | GTT | TTC | GTC | ACA | 338 |
| Asp | Leu | Glu | Asn | Ala | Val | Lys | Asp | Ala | Asn | Met | Leu | Val | Phe | Val | Thr | |
| | | 95 | | | | | 100 | | | | | 105 | | | | |
| CCG | CAT | CAG | TTC | GTG | GAG | GGC | ATC | TGC | AAA | AGA | CTT | GTA | GGG | AAG | ATA | 386 |
| Pro | His | Gln | Phe | Val | Glu | Gly | Ile | Cys | Lys | Arg | Leu | Val | Gly | Lys | Ile | |
| | 110 | | | | | 115 | | | | | 120 | | | | | |
| CAG | GAA | GGA | GCG | CAG | GCT | CTC | TCT | CTT | ATA | AAA | GGC | ATG | GAG | GTC | AAA | 434 |
| Gln | Glu | Gly | Ala | Gln | Ala | Leu | Ser | Leu | Ile | Lys | Gly | Met | Glu | Val | Lys | |
| 125 | | | | | 130 | | | | | 135 | | | | | 140 | |
| ATG | GAG | GGG | CCT | TGC | ATG | ATC | TCG | AGC | CTA | ATC | TCA | GAT | CTT | CTC | GGG | 482 |
| Met | Glu | Gly | Pro | Cys | Met | Ile | Ser | Ser | Leu | Ile | Ser | Asp | Leu | Leu | Gly | |
| | | | | 145 | | | | | 150 | | | | | 155 | | |
| ATC | AAT | TGC | TGT | GTC | CTT | AAT | GGG | GCG | AAC | ATC | GCT | AAT | GAG | ATT | GCT | 530 |
| Ile | Asn | Cys | Cys | Val | Leu | Asn | Gly | Ala | Asn | Ile | Ala | Asn | Glu | Ile | Ala | |
| | | | 160 | | | | | 165 | | | | | 170 | | | |
| GTT | GAG | AAA | TTC | AGT | GAA | GCG | ACT | GTC | GGG | TTC | AGA | GAA | AAT | AGA | GAT | 578 |
| Val | Glu | Lys | Phe | Ser | Glu | Ala | Thr | Val | Gly | Phe | Arg | Glu | Asn | Arg | Asp | |
| | | 175 | | | | | 180 | | | | | 185 | | | | |
| ATT | GCG | GAA | AAA | TGG | GTT | CAG | CTC | TTT | AGC | ACT | CCA | TAC | TTC | ATG | GTC | 626 |
| Ile | Ala | Glu | Lys | Trp | Val | Gln | Leu | Phe | Ser | Thr | Pro | Tyr | Phe | Met | Val | |
| | 190 | | | | | 195 | | | | | 200 | | | | | |
| TCA | GCT | GTT | GAA | GAT | GTT | GAA | GGA | GTA | GAG | CTT | TGT | GGA | ACA | CTG | AAG | 674 |
| Ser | Ala | Val | Glu | Asp | Val | Glu | Gly | Val | Glu | Leu | Cys | Gly | Thr | Leu | Lys | |
| 205 | | | | | 210 | | | | | 215 | | | | | 220 | |
| AAT | ATT | GTG | GCC | ATA | GCA | GCG | GGT | TTT | GTG | GAT | GGA | CTG | GAG | ATG | GGA | 722 |
| Asn | Ile | Val | Ala | Ile | Ala | Ala | Gly | Phe | Val | Asp | Gly | Leu | Glu | Met | Gly | |
| | | | | 225 | | | | | 230 | | | | | 235 | | |
| AAC | AAC | ACA | AAA | GCA | GCA | ATT | ATG | AGG | ATC | GGG | CTG | CGG | GAG | ATG | AAA | 770 |
| Asn | Asn | Thr | Lys | Ala | Ala | Ile | Met | Arg | Ile | Gly | Leu | Arg | Glu | Met | Lys | |
| | | | 240 | | | | | 245 | | | | | 250 | | | |

```
GCG TTC TCC AAG CTT TTG TTT CCA TCT GTT AAG GAC ACT ACT TTT TTC      818
Ala Phe Ser Lys Leu Leu Phe Pro Ser Val Lys Asp Thr Thr Phe Phe
        255                 260                 265

GAG AGC TGC GGA GTC GCT GAT CTC ATC ACA ACT TGT TTG GGC GGA AGA      866
Glu Ser Cys Gly Val Ala Asp Leu Ile Thr Thr Cys Leu Gly Gly Arg
        270                 275                 280

AAC AGA AAA GTC GCT GAG GCT TTT GCA AAG AAT GGC GGT AAC AGG TCA      914
Asn Arg Lys Val Ala Glu Ala Phe Ala Lys Asn Gly Gly Asn Arg Ser
285                 290                 295                 300

TTC GAT GAT CTC GAA GCA GAG ATG CTC CGG GGG CAA AAA TTA CAG GGT      962
Phe Asp Asp Leu Glu Ala Glu Met Leu Arg Gly Gln Lys Leu Gln Gly
                305                 310                 315

GTC TCG ACA GCG AAA GAG GTC TAC GAG GTC CTG AGG CAC CGA GGT TGG     1010
Val Ser Thr Ala Lys Glu Val Tyr Glu Val Leu Arg His Arg Gly Trp
            320                 325                 330

CTC GAG TTG TTC CCG CTC TTC TCA ACC GTG CAT GAG ATC TCC ACT GGC     1058
Leu Glu Leu Phe Pro Leu Phe Ser Thr Val His Glu Ile Ser Thr Gly
                335                 340                 345

CGT CTG CCT CCT TCA GCC ATT GTT GAA TAC AGC GAA CAA AAG CCC ACC     1106
Arg Leu Pro Pro Ser Ala Ile Val Glu Tyr Ser Glu Gln Lys Pro Thr
        350                 355                 360

TTC TCT TGG TAGAGAAAGA AGCAACCAGG AAGAACGGCG AGCCACTCTG             1155
Phe Ser Trp
365

CCTCGTTTAA AGGGTTACTA TTTCTCTACA CTCTGCAGCC TGAAGAGTCG GAAACATCGA   1215

AAATCTAGGA AGTCTCAGAA AAATGAAGGT TTGGAGGATG TATGGATGAT ATATATACTA   1275

GGTGGGTATG AAGAGGAAGT TATTACTATG ATGTTGGTAT GTGGTAATGG CTAAGTACAT   1335

GAGATCAAAT AAATAGACAG ACCTTGGTTT CTTCTATCTC GATTCGGTCT CGTCGAGTTT   1395

GGCGAAACTC AACTGAACTT CCTGAGTACC CTGCTACCTA TTACATGTAA TGTTCCTATT   1455

TATATGCTTA AAAAAAAAAA AAAAAAAAAC TCGAG                              1490

(2) INFORMATION FOR SEQ ID NO:6:

(i) SEQUENCE CHARACTERISTICS:
         (A) LENGTH: 367 amino acids
         (B) TYPE: amino acid
         (D) TOPOLOGY: linear (ii) MOLECULE TYPE: protein (xi) SEQUENCE DESCRIPTION: SEQ ID NO:6:

Leu Asn Ser Ala His Gln Asn Pro His Ser Ser Gly Tyr Glu Gly Pro
  1               5                  10                  15

Arg Ser Arg Val Thr Val Val Gly Ser Gly Asn Trp Gly Ser Val Ala
             20                  25                  30

Ala Lys Leu Ile Ala Ser Asn Thr Leu Lys Leu Pro Ser Phe His Asp
         35                  40                  45

Glu Val Arg Met Trp Val Phe Glu Glu Thr Leu Pro Gly Gly Glu Lys
     50                  55                  60

Leu Thr Asp Ile Ile Asn Gln Thr Asn Glu Asn Val Lys Tyr Leu Pro
 65                  70                  75                  80

Gly Ile Lys Leu Gly Arg Asn Val Val Ala Asp Pro Asp Leu Glu Asn
                 85                  90                  95

Ala Val Lys Asp Ala Asn Met Leu Val Phe Val Thr Pro His Gln Phe
                100                 105                 110

Val Glu Gly Ile Cys Lys Arg Leu Val Gly Lys Ile Gln Glu Gly Ala
            115                 120                 125
```

```
Gln Ala Leu Ser Leu Ile Lys Gly Met Glu Val Lys Met Glu Gly Pro
    130                 135                 140

Cys Met Ile Ser Ser Leu Ile Ser Asp Leu Leu Gly Ile Asn Cys Cys
145                 150                 155                 160

Val Leu Asn Gly Ala Asn Ile Ala Asn Glu Ile Ala Val Glu Lys Phe
                165                 170                 175

Ser Glu Ala Thr Val Gly Phe Arg Glu Asn Arg Asp Ile Ala Glu Lys
            180                 185                 190

Trp Val Gln Leu Phe Ser Thr Pro Tyr Phe Met Val Ser Ala Val Glu
        195                 200                 205

Asp Val Glu Gly Val Glu Leu Cys Gly Thr Leu Lys Asn Ile Val Ala
    210                 215                 220

Ile Ala Ala Gly Phe Val Asp Gly Leu Glu Met Gly Asn Asn Thr Lys
225                 230                 235                 240

Ala Ala Ile Met Arg Ile Gly Leu Arg Glu Met Lys Ala Phe Ser Lys
                245                 250                 255

Leu Leu Phe Pro Ser Val Lys Asp Thr Thr Phe Phe Glu Ser Cys Gly
            260                 265                 270

Val Ala Asp Leu Ile Thr Thr Cys Leu Gly Gly Arg Asn Arg Lys Val
        275                 280                 285

Ala Glu Ala Phe Ala Lys Asn Gly Gly Asn Arg Ser Phe Asp Asp Leu
    290                 295                 300

Glu Ala Glu Met Leu Arg Gly Gln Lys Leu Gln Gly Val Ser Thr Ala
305                 310                 315                 320

Lys Glu Val Tyr Glu Val Leu Arg His Arg Gly Trp Leu Glu Leu Phe
                325                 330                 335

Pro Leu Phe Ser Thr Val His Glu Ile Ser Thr Gly Arg Leu Pro Pro
            340                 345                 350

Ser Ala Ile Val Glu Tyr Ser Glu Gln Lys Pro Thr Phe Ser Trp
        355                 360                 365

(2) INFORMATION FOR SEQ ID NO:7:

(i) SEQUENCE CHARACTERISTICS:
        (A) LENGTH: 1390 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (A) ORGANISM: Cuphea lanceolata (vii) IMMEDIATE SOURCE:
        (A) LIBRARY: ZAP cDNA library
        (B) CLONE: C1GPDH30

(ix) FEATURE:
        (A) NAME/KEY: CDS
        (B) LOCATION: 34..1149

(xi) SEQUENCE DESCRIPTION: SEQ ID NO:7:

GAATTCGGCA CGAGTTTCTT CTCAGCCTCT GCA ATG GCT CCC TCT GAG CTC AAC         54
                                    Met Ala Pro Ser Glu Leu Asn
                                     1               5

TGC ACC CAC CAG AAC CCA CAT TCA AGC GGT TAC GAC GGA CCC AGA TCG         102
```

-continued

```
Cys Thr His Gln Asn Pro His Ser Ser Gly Tyr Asp Gly Pro Arg Ser
        10                  15                  20

AGG GTC ACC GTT GTC GGT AGT GGA AAC TGG GGC AGT GTC GCT GCC AAG      150
Arg Val Thr Val Val Gly Ser Gly Asn Trp Gly Ser Val Ala Ala Lys
 25                  30                  35

CTC ATT GCT TCC AAT ACC CTC AAG CTT CCA TCT TTT CAT GAT GAA GTG      198
Leu Ile Ala Ser Asn Thr Leu Lys Leu Pro Ser Phe His Asp Glu Val
 40                  45                  50                  55

AGA ATG TGG GTA TTT GAG GAG ACT CTA CCG AGC GGC GAG AAG CTT ACT      246
Arg Met Trp Val Phe Glu Glu Thr Leu Pro Ser Gly Glu Lys Leu Thr
                     60                  65                  70

GAT GTC ATC AAC CAG ACC AAT GAA AAT GTT AAG TAT CTC CCC GGA ATT      294
Asp Val Ile Asn Gln Thr Asn Glu Asn Val Lys Tyr Leu Pro Gly Ile
                 75                  80                  85

AAG CTC GGT AGG AAT GTT GTT GCA GAT CCA GAC CTC GAA AAC GCA GTT      342
Lys Leu Gly Arg Asn Val Val Ala Asp Pro Asp Leu Glu Asn Ala Val
             90                  95                 100

AAG GAT GCA AAT ATG CTC GTG TTT GTG ACA CCG CAT CAG TTC ATG GAG      390
Lys Asp Ala Asn Met Leu Val Phe Val Thr Pro His Gln Phe Met Glu
        105                 110                 115

GGC ATC TGC AAA AGA CTC GTA GGG AAA ATA CAG GAA GGA GCA CAG GCT      438
Gly Ile Cys Lys Arg Leu Val Gly Lys Ile Gln Glu Gly Ala Gln Ala
120                 125                 130                 135

CTC TCC CTT ATA AAG GGC ATG GAG GTC AAA ATG GAG GGG CCT TGC ATG      486
Leu Ser Leu Ile Lys Gly Met Glu Val Lys Met Glu Gly Pro Cys Met
                140                 145                 150

ATC TCG AGC CTA ATC TCT GAT CTT CTC GGG ATC AAC TGC TGT GTC CTA      534
Ile Ser Ser Leu Ile Ser Asp Leu Leu Gly Ile Asn Cys Cys Val Leu
            155                 160                 165

ATG GGG GCA AAC ATC GCT AAT GAG ATT GCT GTT GAG AAA TTC AGT GAA      582
Met Gly Ala Asn Ile Ala Asn Glu Ile Ala Val Glu Lys Phe Ser Glu
        170                 175                 180

GCG ACA GTC GGG TTC AGA GAA AAT ACA GAT ATT GCG GAG AAA TGG GTT      630
Ala Thr Val Gly Phe Arg Glu Asn Thr Asp Ile Ala Glu Lys Trp Val
185                 190                 195

CAG CTC TTT AGC ACT CCG TAC TTC ATG GTC TCA GCT GTT GAA GAT GTT      678
Gln Leu Phe Ser Thr Pro Tyr Phe Met Val Ser Ala Val Glu Asp Val
200                 205                 210                 215

GAA GGA GTA GAA CTT TGT GGA ACA CTG AAG AAT ATC GTG GCC ATA GCA      726
Glu Gly Val Glu Leu Cys Gly Thr Leu Lys Asn Ile Val Ala Ile Ala
                220                 225                 230

GCC GGT TTT GTG GAT GGA TTG GAG ATG GGA AAC AAC ACA AAA GCA GCA      774
Ala Gly Phe Val Asp Gly Leu Glu Met Gly Asn Asn Thr Lys Ala Ala
            235                 240                 245

ATT ATG AGG ATC GGG TTA CGG GAG ATG AAG GCA TTC TCC AAG CTT TTG      822
Ile Met Arg Ile Gly Leu Arg Glu Met Lys Ala Phe Ser Lys Leu Leu
        250                 255                 260

TTT CCA TCT GTT AAG GAC ACT ACT TTC TTC GAG AGC TGT GGA GTT GCT      870
Phe Pro Ser Val Lys Asp Thr Thr Phe Phe Glu Ser Cys Gly Val Ala
265                 270                 275

GAC CTC ATC ACA ACT TGT TTG GGC GGG AGA AAC AGA AAA GTT GCT GAG      918
Asp Leu Ile Thr Thr Cys Leu Gly Gly Arg Asn Arg Lys Val Ala Glu
280                 285                 290                 295

GCT TTT GCA AAG AAT GGC GGG GAA AGG TCA TTC GAT GAT CTC GAA GCA      966
Ala Phe Ala Lys Asn Gly Gly Glu Arg Ser Phe Asp Asp Leu Glu Ala
                300                 305                 310

GAG CTG CTC CGG GGG CAA AAA TTA CAG GGT GTC TCA ACA GCA AAG GAG     1014
Glu Leu Leu Arg Gly Gln Lys Leu Gln Gly Val Ser Thr Ala Lys Glu
            315                 320                 325
```

```
GTC TAT GAA GTC TTG GGG CAC CGA GGC TGG CTC GAG CTG TTC CCG CTC     1062
Val Tyr Glu Val Leu Gly His Arg Gly Trp Leu Glu Leu Phe Pro Leu
        330                 335                 340

TTC TCA ACC GTG CAC GAG ATC TCC ACT GGC CGT CTG CAT CCT TCA GCC     1110
Phe Ser Thr Val His Glu Ile Ser Thr Gly Arg Leu His Pro Ser Ala
345                 350                 355

ATC GTC GAA TAC AGC GAA CAA AAA ACC ATC TTC TCT TGG TAGAGCAAGA      1159
Ile Val Glu Tyr Ser Glu Gln Lys Thr Ile Phe Ser Trp
360                 365                 370

GGCTGCCCTT GAAAGACTAA GAGCCACCCT GCCCTGTTTA AAGGGCTAAA AGTTTAATAT   1219

TTCTCTGCAG CCTAAACAGT TGGAAACATT GAAAATCTAG GATGTATCAG AAAAAAGAAG   1279

GTTTGGAGGA AGTATGGATG ATATAGAGGA CATGAATGTA TTCATTTTCG GTATACTCTT   1339

TTTCTGCAAA ATAATTCTTC AGATGTAAAA AAAAAAAAAA AAAACTCGA G             1390
```

(2) INFORMATION FOR SEQ ID NO:8:

(i) SEQUENCE CHARACTERISTICS:
        (A) LENGTH: 372 amino acids
        (B) TYPE: amino acid
        (D) TOPOLOGY: linear (ii) MOLECULE TYPE: protein (xi) SEQUENCE DESCRIPTION: SEQ ID NO:8:

```
Met Ala Pro Ser Glu Leu Asn Cys Thr His Gln Asn Pro His Ser Ser
1               5                   10                  15

Gly Tyr Asp Gly Pro Arg Ser Arg Val Thr Val Gly Ser Gly Asn
            20                  25                  30

Trp Gly Ser Val Ala Ala Lys Leu Ile Ala Ser Asn Thr Leu Lys Leu
            35                  40                  45

Pro Ser Phe His Asp Glu Val Arg Met Trp Val Phe Glu Glu Thr Leu
        50                  55                  60

Pro Ser Gly Glu Lys Leu Thr Asp Val Ile Asn Gln Thr Asn Glu Asn
65                  70                  75                  80

Val Lys Tyr Leu Pro Gly Ile Lys Leu Gly Arg Asn Val Val Ala Asp
                85                  90                  95

Pro Asp Leu Glu Asn Ala Val Lys Asp Ala Asn Met Leu Val Phe Val
            100                 105                 110

Thr Pro His Gln Phe Met Glu Gly Ile Cys Lys Arg Leu Val Gly Lys
            115                 120                 125

Ile Gln Glu Gly Ala Gln Ala Leu Ser Leu Ile Lys Gly Met Glu Val
        130                 135                 140

Lys Met Glu Gly Pro Cys Met Ile Ser Ser Leu Ile Ser Asp Leu Leu
145                 150                 155                 160

Gly Ile Asn Cys Cys Val Leu Met Gly Ala Asn Ile Ala Asn Glu Ile
                165                 170                 175

Ala Val Glu Lys Phe Ser Glu Ala Thr Val Gly Phe Arg Glu Asn Thr
            180                 185                 190

Asp Ile Ala Glu Lys Trp Val Gln Leu Phe Ser Thr Pro Tyr Phe Met
            195                 200                 205

Val Ser Ala Val Glu Asp Val Glu Gly Val Glu Leu Cys Gly Thr Leu
        210                 215                 220

Lys Asn Ile Val Ala Ile Ala Ala Gly Phe Val Asp Gly Leu Glu Met
225                 230                 235                 240

Gly Asn Asn Thr Lys Ala Ala Ile Met Arg Ile Gly Leu Arg Glu Met
                245                 250                 255
```

```
Lys Ala Phe Ser Lys Leu Leu Phe Pro Ser Val Lys Asp Thr Thr Phe
        260                 265                 270
Phe Glu Ser Cys Gly Val Ala Asp Leu Ile Thr Thr Cys Leu Gly Gly
        275                 280                 285
Arg Asn Arg Lys Val Ala Glu Ala Phe Ala Lys Asn Gly Gly Glu Arg
        290                 295                 300
Ser Phe Asp Asp Leu Glu Ala Glu Leu Leu Arg Gly Gln Lys Leu Gln
305                 310                 315                 320
Gly Val Ser Thr Ala Lys Glu Val Tyr Glu Val Leu Gly His Arg Gly
                325                 330                 335
Trp Leu Glu Leu Phe Pro Leu Phe Ser Thr Val His Glu Ile Ser Thr
            340                 345                 350
Gly Arg Leu His Pro Ser Ala Ile Val Glu Tyr Ser Glu Gln Lys Thr
        355                 360                 365
Ile Phe Ser Trp
    370
```

(2) INFORMATION FOR SEQ ID NO:9:

(i) SEQUENCE CHARACTERISTICS:
        (A) LENGTH: 4434 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Cuphea lanceolata (vii) IMMEDIATE SOURCE:
        (A) LIBRARY: Genomic lambda FIX II
        (B) CLONE: C1GPDHg5

(ix) FEATURE:
        (A) NAME/KEY: CDS
        (B) LOCATION: join(1394..1550, 2066..2142, 2241..2313, 2405
          ..2622, 2719..2826, 2961..3024, 3223..3260, 3342
          ..3462, 3541..3595, 3692..3740, 3850..4005)

(xi) SEQUENCE DESCRIPTION: SEQ ID NO:9:

```
GGATCCTTAG AAGACAAGCG CGGGGCGGGC ATGGGTCTCG TGATACCCGC CCCATTTTGC      60

CCCATTCCAT CCCTATATGG TAAGCAGATC TCACTGAAAA GTCACCGTTT CTGGATGGTT     120

TCCAGATGAT TTTGTCCCTC CCTCTAGCTG CATTAGGTGA TGGGATTGAG GCTATTCTAA     180

GAACCAGCTC GTGTGGAAGG TAGGCGGAGA TTAGCTCCCA GTTCCATCCT CCTGTATTTG     240

AAGCGAAGAA AGAAACTGGG TTGTCTAGCA TGTTTTGTGG GACAGGTTTG GTCGTCTTTT     300

CTGATAGGCT CTGATTCAAT AGAAGCCAAT TATCTCTCCA AAAGGAAACC TTATTACCAC     360

TTCCAATCGA CCACCCTATG TACTTGCTGA TCTTCGGCCA GGTATCGCAT AAAGCATTCC     420

ATAACGCTGA TGCTGTCGTC TTTTTTGTGA ATGTTGGCAA GAGTGTGTCT GGCATGGCAT     480

ATTTGTGACT GAGCACCCGC ACCCAAAGGC TCTGAGGTTG TGATGCCATA TCCCAACATA     540

CCTTCGATAG AAAGGCTTCA TTCATCTTCC GTAGCTTACG AATGCCAAGA CCACCCCATG     600

GTGCTGGACT AGTGACCGTG GACCAATTGA CCAAATGCAC CTTCCTTTGC TCCATTGAAT     660

GGCCCCAAAT GAAGTTGCCG CAATGTCTTT CGATTTCATC AAGTGTTCCA TGAGGAATAC     720
```

```
GTGTGGACTG CATGGAGAAG GATGGCAGAG CCGTCAAGAC AGATTTCACC AGCGTCACCC        780

GCCCAGCCAT TGACAGTGTC GATGCCGACC AACCAGCAAG TCTTGCTTTT ACCTCGACAT        840

GTTTTGGATT TTATATACCG GTGGTGATGG TGTTTGAATT AATCATCGTC ATTAATTTAT        900

ACCGTGCAAT ATATATTGCA ACATTCCAAA GTATAATTAA TTTTATATGT CCATTCGTGA        960

CTAATCTTGG AGATAGGGCT TAAATTGTTA TATGATGATA TAGAAGAAGT TGGATAGCAC       1020

ATAAGAACTC TATAAAATGC TTATAGATCA TGGCATCGAA TTCATCCGCT ATATATGAGT       1080

GAGGAAGAAA CTAATCAAAA CCTCGTATTC ATCGAAACAA CCGTTGAAGT GGTTACACTT       1140

TGAATCCTAA GACATACTTG ACGTCATGAT TCTGTCTCTC TATTCCATTG CATAATAAAT       1200

AAAACAAAGG AAACAAAAGC ATAGAGGAGA TCGCCAGATT CAGCAGTTTC CGCATAGGTT       1260

GCCACGGAGC CTTACATGCC GATGCCTTCC TCTGCCTCCT TCTTCCTCCT GTCTCTCTCT       1320

CTACATCCCC TTATATCCCT TCCTCCTTCC CTCCATCTTC ACCATTCCTC TGTTTTCTT        1380

CTCAGCCTCT GCA ATG GCT CCC TCT GAG CTC AAC TGC ACC CAC CAG AAC         1429
            Met Ala Pro Ser Glu Leu Asn Cys Thr His Gln Asn
              1               5                   10

CCA CAT TCA AGC GGT TAC GAC GGA CCC AGA TCG AGG GTC ACC GTT GTC        1477
Pro His Ser Ser Gly Tyr Asp Gly Pro Arg Ser Arg Val Thr Val Val
           15                  20                  25

GGT AGT GGA AAC TGG GGC AGT GTC GCT GCC AAG CTC ATT GCT TCC AAT        1525
Gly Ser Gly Asn Trp Gly Ser Val Ala Ala Lys Leu Ile Ala Ser Asn
 30                  35                  40

ACC CTC AAG CTT CCA TCT TTT CAT  G GTTCGTCTCT CCTTTTCTCT               1570
Thr Leu Lys Leu Pro Ser Phe His
 45                  50

GAAAAATGAA GCTTTTGCAT GGGATAGTCA CTAGATATGA GCCTCTGTTT GCATGACTGA       1630

AGCGCTTGAG TAACCGAGTT TTTGGAACAA GAGCACAGGT GGTTCCTTTG CATTTTCTTT       1690

GAGGTTCCTT AATCATTCAA TGAAGTAGCG GTTGATCGCT GAGCAATTGA AACTTGTGGA       1750

ATCGAACCTC CAGCCGAGTC TTAGTGTAAT TGCTTTCTGT TTTACTTCAT TCATAGTGGG       1810

AAGGAGTACG AACTGATGAG TGATGTCACA TTTCATTAGT CGGGTTGCGA AAAAACTCAG       1870

TTGACATATT GGTCGAGACT CTGCAGTGTC ATCAGATATG AGTTGGTGTA TTTGTATTGA       1930

CATTTGAATT TGGTATGTGT ATGAATTTTG TTGAATTAAT CACCGCTGTG ATGAAAAGAT       1990

CAGTACTTCT TCGGTCATTT TTCAGGTGGA AGGATGTTGG TTTCTTATAT ATGTAACTTT       2050

ACATGAATTT TTCAG AT GAA GTG AGA ATG TGG GTA TTT GAG GAG ACT CTA        2100
               Asp Glu Val Arg Met Trp Val Phe Glu Glu Thr Leu
                              55                  60

CCG AGC GGC GAG AAG CTT ACT GAT GTC ATC AAC CAG ACC AAT                2142
Pro Ser Gly Glu Lys Leu Thr Asp Val Ile Asn Gln Thr Asn
 65                  70                  75

GTAAGGAAAC ACAGATTAGC AATAGCATGA GCAGTTATTG CTGGTTAAAT ATGCTTGTTA       2202

GCAACTTTCG TGACGGCCTG AGTTTTATAC CTCTGCAG GAA AAT GTT AAG TAT          2255
                                          Glu Asn Val Lys Tyr
                                                    80

CTC CCC GGA ATT AAG CTC GGT AGG AAT GTT GTT GCA GAT CCA GAC CTC        2303
Leu Pro Gly Ile Lys Leu Gly Arg Asn Val Val Ala Asp Pro Asp Leu
      85                  90                  95

GAA AAC GCA  G GTAGTCCATG TGTTCATTAG AATTCTCTAA TTAATTATTG             2353
Glu Asn Ala
100

TGGTTTATTT CCTTGTCTCT GTGATGATAT TCTGGATGAA ATTTTGTGCA G  TT AAG       2409
                                                         Val Lys
```

```
GAT GCA AAT ATG CTC GTG TTT GTG ACA CCG CAT CAG TTC ATG GAG GGC       2457
Asp Ala Asn Met Leu Val Phe Val Thr Pro His Gln Phe Met Glu Gly
105                 110                 115                 120

ATC TGC AAA AGA CTC GTA GGG AAA ATA CAG GAA GGA GCA CAG GCT CTC       2505
Ile Cys Lys Arg Leu Val Gly Lys Ile Gln Glu Gly Ala Gln Ala Leu
                125                 130                 135

TCC CTT ATA AAG GGC ATG GAG GTC AAA ATG GAG GGG CCT TGC ATG ATC       2553
Ser Leu Ile Lys Gly Met Glu Val Lys Met Glu Gly Pro Cys Met Ile
            140                 145                 150

TCG AGC CTA ATC TCT GAT CTT CTC GGG ATC AAC TGC TGT GTC CTA ATG       2601
Ser Ser Leu Ile Ser Asp Leu Leu Gly Ile Asn Cys Cys Val Leu Met
        155                 160                 165

GGG GCA AAC ATC GCT AAT GAG GTAAACACTT GGCACGATCT GGTTGCAACT          2652
Gly Ala Asn Ile Ala Asn Glu
    170                 175

CCCCCAGGAA ATTGTAGATC CTATACTGT TAGCATCTTG ATGAGGTTAA ATATCTTATG      2712

TTGTAG ATT GCT GTT GAG AAA TTC AGT GAA GCG ACA GTC GGG TTC AGA        2760
       Ile Ala Val Glu Lys Phe Ser Glu Ala Thr Val Gly Phe Arg
                       180                 185

GAA AAT ACA GAT ATT GCG GAG AAA TGG GTT CAG CTC TTT AGC ACT CCG       2808
Glu Asn Thr Asp Ile Ala Glu Lys Trp Val Gln Leu Phe Ser Thr Pro
190                 195                 200                 205

TAC TTC ATG GTC TCA GCT GTAAGTTGCG ATAAAACCTT ACGTTTTGCT              2856
Tyr Phe Met Val Ser Ala
            210

AATAGAACAC AATGCTAGAA ACTCCCAGAT TTCAATGTTA TGTATTTTGG TGCCCAAAGA     2916

AGCAACTTCT TAACATCTGT GGCTCCTCTT ACTGACAAAA ATAG GTT GAA GAT GTT      2972
                                                 Val Glu Asp Val
                                                              215

GAA GGA GTA GAA CTT TGT GGA ACA CTG AAG AAT ATC GTG GCC ATA GCA       3020
Glu Gly Val Glu Leu Cys Gly Thr Leu Lys Asn Ile Val Ala Ile Ala
                220                 225                 230

GCC  G GTTCGTGTTT ACGAGATGTA CATTTATGTA TAACAATCTT TCATTTATTC         3074
Ala

ATCGAGATGG GATGCAATAT ATCAATGAGA GGGAAAAGAA AGGGCAAAGG AAAATGCTGT     3134

TGTATTGCAG CTTTAGGCAT TCTTTTCTCT TAATTATTAA CTGTGAAACA CCGAGAAGTA     3194

TTGATGAAGT TAAGAAACGA TGTTACAG  GT TTT GTG GAT GGA TTG GAG ATG        3245
                                Gly Phe Val Asp Gly Leu Glu Met
                                            235                 240

GGA AAC AAC ACA AAA GTAAGTCTAA ATTTTTTGTA AAACTTAAAG TAAGAGTTTA       3300
Gly Asn Asn Thr Lys
                245

TGCTTTGGCA TTGTTTGAAG TTCACTTACT AATGACTTTA G GCA GCA ATT ATG         3353
                                              Ala Ala Ile Met

AGG ATC GGG TTA CGG GAG ATG AAG GCA TTC TCC AAG CTT TTG TTT CCA       3401
Arg Ile Gly Leu Arg Glu Met Lys Ala Phe Ser Lys Leu Leu Phe Pro
250                 255                 260                 265

TCT GTT AAG GAC ACT ACT TTC TTC GAG AGC TGT GGA GTT GCT GAC CTC       3449
Ser Val Lys Asp Thr Thr Phe Phe Glu Ser Cys Gly Val Ala Asp Leu
                270                 275                 280

ATC ACA ACT TGT  T GTAAGGAAGC ATATAGATTT CCTTCGAATA TGAATAAATT        3502
Ile Thr Thr Cys
            285

GCATAGTTCA TATCATCATA ATTTGTGTTT GTGCTCAG  TG GGC GGG AGA AAC         3554
                                            Leu Gly Gly Arg Asn
                                                            290

AGA AAA GTT GCT GAG GCT TTT GCA AAG AAT GGC GGG GAA  AG              3595
```

-continued

```
Arg Lys Val Ala Glu Ala Phe Ala Lys Asn Gly Gly Glu  Arg
            295                 300

GTCGTGTTTC CCTTTCGTCG ATCCTGATTT AATTCCTGTT TAGTGGTATT CACTTTGTGT      3655

GTATGTAAAT CAAGCAACTA TTTCCATCAT CTTCAG G TCA TTC GAT GAT CTC          3707
                                          Ser Phe Asp Asp Leu
                                                      305

GAA GCA GAG CTG CTC CGG GGG CAA AAA TTA CAG GTACATGATG AAGAAACCGA      3760
Glu Ala Glu Leu Leu Arg Gly Gln Lys Leu Gln
310                 315                 320

TGTCTATACA GAAAGAGTCC ATTGCAAAGC TTGAGAATGT TCGAGCATA AAGAGCATAA       3820

GAATATTCTT TTCGGTGATT TTCATGCAG GGT GTC TCA ACA GCA AAG GAG GTC        3873
                                 Gly Val Ser Thr Ala Lys Glu Val
                                                         325

TAT GAA GTC TTG GGG CAC CGA GGC TGG CTC GAG CTG TTC CCG CTC TTC        3921
Tyr Glu Val Leu Gly His Arg Gly Trp Leu Glu Leu Phe Pro Leu Phe
    330                 335                 340

TCA ACC GTG CAC GAG ATC TCC ACT GGC CGT CTG CAT CCT TCA GCC ATC        3969
Ser Thr Val His Glu Ile Ser Thr Gly Arg Leu His Pro Ser Ala Ile
345                 350                 355                 360

GTC GAA TAC AGC GAA CAA AAA ACC ATC TTC TCT TGG TAGAGCAAGA             4015
Val Glu Tyr Ser Glu Gln Lys Thr Ile Phe Ser Trp
            365                 370

GGCTGCCCTT GAAAGACTAA GAGCCACCCT GCCCTGTTTA AAGGGCTAAA AGTTTAATAT      4075

TTCTCTGCAG CCTAAACAGT TGGAAACATT GAAAATCTAG GATGTATCAG AAAAAAGAAG      4135

GTTTGGAGGA AGTATGGATG ATATAGAGGA CATGAATGTA TTCATTTTCG GTATACTCTT      4195

TTTCTGCAAA ATAATTCTTC AGATGTTTTT GTGGTATGAG ATATAGAGGA CATGTATGTA      4255

TGCGGTAAGG CTGAAGTAAA CAAGTTACCA TAAGAGACAG CCCTCTCGGT TTCTTCCATC      4315

TGATCGATTC GTCTCGTCGA ATTTGCCAAA AGCTCAAAAC TCAACTCATC CCCTGCTTTC      4375

TATCCATATG GGCAAGGAAT ACAATTAGAC CAGTTTGATA CTTGTAATGA AAGTTTAC        4434

(2) INFORMATION FOR SEQ ID NO:10:

(i) SEQUENCE CHARACTERISTICS:
        (A) LENGTH: 372 amino acids
        (B) TYPE: amino acid
        (D) TOPOLOGY: linear (ii) MOLECULE TYPE: protein (xi) SEQUENCE DESCRIPTION: SEQ ID NO:10:

Met Ala Pro Ser Glu Leu Asn Cys Thr His Gln Asn Pro His Ser Ser
1               5                  10                  15

Gly Tyr Asp Gly Pro Arg Ser Arg Val Thr Val Gly Ser Gly Asn
            20                  25                  30

Trp Gly Ser Val Ala Ala Lys Leu Ile Ala Ser Asn Thr Leu Lys Leu
        35                  40                  45

Pro Ser Phe His Asp Glu Val Arg Met Trp Val Phe Glu Glu Thr Leu
    50                  55                  60

Pro Ser Gly Glu Lys Leu Thr Asp Val Ile Asn Gln Thr Asn Glu Asn
65                  70                  75                  80

Val Lys Tyr Leu Pro Gly Ile Lys Leu Gly Arg Asn Val Ala Asp
            85                  90                  95

Pro Asp Leu Glu Asn Ala Val Lys Asp Ala Asn Met Leu Val Phe Val
            100                 105                 110

Thr Pro His Gln Phe Met Glu Gly Ile Cys Lys Arg Leu Val Gly Lys
```

```
                115                 120                 125
Ile Gln Glu Gly Ala Gln Ala Leu Ser Leu Ile Lys Gly Met Glu Val
130                 135                 140

Lys Met Glu Gly Pro Cys Met Ile Ser Ser Leu Ile Ser Asp Leu Leu
145                 150                 155                 160

Gly Ile Asn Cys Cys Val Leu Met Gly Ala Asn Ile Ala Asn Glu Ile
                165                 170                 175

Ala Val Glu Lys Phe Ser Glu Ala Thr Val Gly Phe Arg Glu Asn Thr
                180                 185                 190

Asp Ile Ala Glu Lys Trp Val Gln Leu Phe Ser Thr Pro Tyr Phe Met
                195                 200                 205

Val Ser Ala Val Glu Asp Val Glu Gly Val Glu Leu Cys Gly Thr Leu
210                 215                 220

Lys Asn Ile Val Ala Ile Ala Ala Gly Phe Val Asp Gly Leu Glu Met
225                 230                 235                 240

Gly Asn Asn Thr Lys Ala Ala Ile Met Arg Ile Gly Leu Arg Glu Met
                245                 250                 255

Lys Ala Phe Ser Lys Leu Leu Phe Pro Ser Val Lys Asp Thr Thr Phe
                260                 265                 270

Phe Glu Ser Cys Gly Val Ala Asp Leu Ile Thr Thr Cys Leu Gly Gly
                275                 280                 285

Arg Asn Arg Lys Val Ala Glu Ala Phe Ala Lys Asn Gly Gly Glu Arg
290                 295                 300

Ser Phe Asp Asp Leu Glu Ala Glu Leu Leu Arg Gly Gln Lys Leu Gln
305                 310                 315                 320

Gly Val Ser Thr Ala Lys Glu Val Tyr Glu Val Leu Gly His Arg Gly
                325                 330                 335

Trp Leu Glu Leu Phe Pro Leu Phe Ser Thr Val His Glu Ile Ser Thr
                340                 345                 350

Gly Arg Leu His Pro Ser Ala Ile Val Glu Tyr Ser Glu Gln Lys Thr
                355                 360                 365

Ile Phe Ser Trp
370

(2) INFORMATION FOR SEQ ID NO:11:

(i) SEQUENCE CHARACTERISTICS:
        (A) LENGTH: 2955 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Cuphea lanceolata (vii) IMMEDIATE SOURCE:
        (A) LIBRARY: Genomic lambda FIX II
        (B) CLONE: C1GPDHg3

(ix) FEATURE:
        (A) NAME/KEY: CDS
        (B) LOCATION: join(1182..1326, 1837..1913, 2010..2082, 2180
            ..2397, 2480..2587, 2668..2731, 2848..2885, 2947
            ..2955)

(xi) SEQUENCE DESCRIPTION: SEQ ID NO:11:
```

-continued

```
GGATCCTCCT CGATGGTGGT CCAATGAAGA CTATACAAAA CCAAGCCGAC GGAATCCGGT      60

GCACAATAAC TTGAAGCCAT GAAAACCAAT GCAATATATA GAGTACGCCT TGTACTATGT     120

AATATATTTA CAATTTTCTC TTGAATAGTT TAGGTTTGGT GATCGTAAAC TCGCAAAACA     180

CATATGTGCG TGTGTAAATA TATCTGGTGA TGATGTATGA AGAGAGTGCG GTTTAATTAC     240

CCGGTATTGT ATAAGGTTGT ATCTGCAGTT GACACTTTCA GTAGAAATTA CTAATAACTC     300

GACGAGATAC AAACGACTCG AGTTTCAGAA ATAAGTGGCA AAACGTTATG GGGTTCTCCT     360

TGATTCTTCG TGGAAGGTAT ACTATTAATC ATGTTCGCCT CCGTCCTAGT AGAAACATAG     420

AGTTTTTATC GGGATGCAGA TTGCAGATGA TAGAACTATT GTCAGATTCA TTATGCATAT     480

AGGATAGGCC TTCTACTGAT TTGGAAACTT ATATCGATTC TGTTGGAATG GATGTATGAA     540

AAGCTTCATA TCCGACATTG AAAATTTGGT CATATCAATA AGATGAACTA ACAAAATATG     600

CCAACCTCTT GGAAGCAAAA CACATCCGAG ACTTTAAGAT GTGGCTGAGG TTTCTGCAAC     660

TTTAAATCTC CCATATGCTT GACAGAATTG GTAGACCTAA CTCAATGGAT TTCATTCAAT     720

GATCGAAGTT TCTCTATCGA TCATAGCTGT GAATTAGTAA GCAAATGTCC ATAATATATC     780

CCCGAAAACA CGTAAAGTTA GGTCTCATTA CATTAGGCCT CAACCATATG TTATAAGTAA     840

ATTTGTTTTT TTTTTTTTCT CTTACAGTTG AATGTATCAA ATCGAAAAAA CCGTTAAGTC     900

GTTGCGGCCC TTTGAATAGT AAGCCAAAGA TCCGAAAGAA AAAGTAAACA GAGACAGAGC     960

AATGAGGAGA TGGCCAGTTT GAGAAGCAAA CGCATAGGTT GCCACGGAGG AGGCGGAGAC    1020

GGGTCATCGA TGACTTTCTC CGCCTCCTTA ACCGCAATGG CGATGCCGCC ATACCTCTCT    1080

GTCACCCTCT CTCCATTCCC TTTATATCTC TCCCGCTTCT TCCTCTGCTC CACTCAACCC    1140

CCTCTGCATA AACTCTGTGC TTTTTTAGTC TCTCCCCTGC T ATG TCG CCG GCA        1193
                                              Met Ser Pro Ala
                                                1

TTC GAA CCC CAT CAG CAG AAG CCT ACC ATG GAG AAC ATG CGA TTC CGA      1241
Phe Glu Pro His Gln Gln Lys Pro Thr Met Glu Asn Met Arg Phe Arg
  5              10                  15                  20

GTC ACC ATC ATT GGC AGC GGT AAC TGG GGC AGC GTC GCC GCT AAG CTC      1289
Val Thr Ile Ile Gly Ser Gly Asn Trp Gly Ser Val Ala Ala Lys Leu
              25                  30                  35

ATT GCC TCC AAC ACC CTC AAC CTC CCG TCT TTC CAC  G GTTTGTCTGC        1336
Ile Ala Ser Asn Thr Leu Asn Leu Pro Ser Phe His
          40                  45

CACTCTTCTT TCTTCATGAT CAGGCTCTTG CCAGTAGAGA CATGTCTTTT CATGAATCAA    1396

GCACCCGTTT TTTCGATGAG ATCACTGAG TTTGATTTAA GGGTATCCGA TGCAACTGCT     1456

GAAAAGATGT GGTTATTTTT GTTCTTTCAT GAAGTATCAT CTGAGAAATT TGATCTTAGC    1516

CTAAGCGGCA TTACTTTCGG TGTTAAGTTC ATTCTATGTG AGTAGGAGTA TGAGGTGATG    1576

CCGCGTGATT CCAATCAGGT ACCGATGAAA ATCAGTAGAC ATGGTTGCAG TTGAGGTTCC    1636

ATAGTTTACA CAGCATAGGA GTTGCTGTAT TTCTATTGAC GCTTGGATTT GTTTGGTGCT    1696

TATAATCCCG GTTTTACTA ATTGGTTATG AACACCGATA ATAACAACAG TTAGATTTCT     1756

TCAACATTAA CCGGTTGAAG ATTAGGCCAT ATTCTTATTT GGGTACTATT TCTTAAGAAA    1816

ACATTCATAT TTTCTTTCAG  AT GAA GTA AGG ATG TGG GTG TTT GAG GAG        1865
                       Asp Glu Val Arg Met Trp Val Phe Glu Glu
                             50                  55

ACA TTG CCA AGC GGC GAG AAG CTC ACT GAA GTC ATC AAC CGG ACC AAT      1913
Thr Leu Pro Ser Gly Glu Lys Leu Thr Glu Val Ile Asn Arg Thr Asn
 60                  65                  70
```

-continued

```
GTAAGGAAGA TCAATTTAGC ATGTCATTGT ATTAACATAA AGAGCGTTTA TTGGCAACTT       1973

TGGCTTTCAT GATGTTCGAG TGTTGCGTCT TTGCAG GAA AAT GTT AAG TAT CTG        2027
                                        Glu Asn Val Lys Tyr Leu
                                         75                  80

CCT GGA TTC AAG CTT GGC AGA AAT GTT ATT GCA GAC CCA AAC CTT GAA        2075
Pro Gly Phe Lys Leu Gly Arg Asn Val Ile Ala Asp Pro Asn Leu Glu
                 85                  90                  95

AAT GCA  G GTAGTGATTG TATTTCAGTG CTCGGTTGAA TGATCAAGTA AAATCCTCGT      2132
Asn Ala

GCTAAATATG TCGAGATGTT CGTGTTTTTG CATAATGTTT TGTTTAG  TT AAG GAA        2187
                                                     Val Lys Glu
                                                             100

GCA AAC ATG CTT GTA TTT GTC ACA CCG CAT CAG TTC GTG GAG GGC CTT        2235
Ala Asn Met Leu Val Phe Val Thr Pro His Gln Phe Val Glu Gly Leu
             105                 110                 115

TGC AAG AGA CTC GTC GGG AAG ATA AAG GCA GGT GCA GAG GCT CTC TCC        2283
Cys Lys Arg Leu Val Gly Lys Ile Lys Ala Gly Ala Glu Ala Leu Ser
         120                 125                 130

CTT ATA AAG GGC ATG GAG GTC AAA AGG GAA GGG CCT TCC ATG ATA TCT        2331
Leu Ile Lys Gly Met Glu Val Lys Arg Glu Gly Pro Ser Met Ile Ser
     135                 140                 145

ACC TTA ATC TCG AGC CTT CTC GGG ATC AAC TGC TGT GTC CTA ATG GGA        2379
Thr Leu Ile Ser Ser Leu Leu Gly Ile Asn Cys Cys Val Leu Met Gly
150                 155                 160                 165

GCA AAC ATC GCC AAC GAG GTAAAATCTT GGTGCAGTCT TACGAGATTC               2427
Ala Asn Ile Ala Asn Glu
                170

TGAATCTTGA ACCTGTTAGC ATTTTGACAC ACTGTGACTT CTAAATTTGT AG ATT          2482
                                                         Ile

GCT CTT GAG AAA TTC AGT GAG GCG ACA GTC GGA TAC AGA GAA AAT AAG        2530
Ala Leu Glu Lys Phe Ser Glu Ala Thr Val Gly Tyr Arg Glu Asn Lys
             175                 180                 185

GAT ACT GCA GAG AAA TGG GTT CGG CTC TTC AAC ACT CCA TAC TTC CAA        2578
Asp Thr Ala Glu Lys Trp Val Arg Leu Phe Asn Thr Pro Tyr Phe Gln
         190                 195                 200

GTC TCG TCT GTGAGTACGA ATAAACCTTT CCTTCTGCGA ACAAAAAACT                2627
Val Ser Ser
205

TCCCGAGGCA GGAACTAAAT GAAACAAGTT AACATAATAG GTT CAA GAT GTG GAA        2682
                                              Val Gln Asp Val Glu
                                                          210

GGA GTG GAA CTT TGT GGC ACA CTG AAG AAT GTC GTG GCC ATA GCA GCC  G     2731
Gly Val Glu Leu Cys Gly Thr Leu Lys Asn Val Val Ala Ile Ala Ala
             215                 220                 225

GTACTTATAT ACGATCTCCA CATTTATATA AACTAGTTAG AAAGATTTTG GATTGCTGTA      2791

AAAACCGTGG AAAAACCCGA AAAGTGTTGA TGAAGTGTTA CCAAATGTTG TTTCAG  GT      2849
                                                                Gly

TTT GTA GAT GGA CTG GAG ATG GGA AAC AAC ACA AAG GTAAGTCCAA             2895
Phe Val Asp Gly Leu Glu Met Gly Asn Asn Thr Lys
230                 235                 240

AGTTCATGCA AATTTTTTCG TATTTACGAC TGAATGCTTG GATATACATA G GCT GCG       2952
                                                         Ala Ala

ATT                                                                    2955
Ile
```

(2) INFORMATION FOR SEQ ID NO:12:

(i) SEQUENCE CHARACTERISTICS:

(A) LENGTH: 244 amino acids
              (B) TYPE: amino acid
              (D) TOPOLOGY: linear (ii) MOLECULE TYPE: protein (xi) SEQUENCE DESCRIPTION: SEQ ID NO:12:

Met Ser Pro Ala Phe Glu Pro His Gln Gln Lys Pro Thr Met Glu Asn
1               5                   10                  15

Met Arg Phe Arg Val Thr Ile Ile Gly Ser Gly Asn Trp Gly Ser Val
            20                  25                  30

Ala Ala Lys Leu Ile Ala Ser Asn Thr Leu Asn Leu Pro Ser Phe His
            35                  40                  45

Asp Glu Val Arg Met Trp Val Phe Glu Glu Thr Leu Pro Ser Gly Glu
        50                  55                  60

Lys Leu Thr Glu Val Ile Asn Arg Thr Asn Glu Asn Val Lys Tyr Leu
65                  70                  75                  80

Pro Gly Phe Lys Leu Gly Arg Asn Val Ile Ala Asp Pro Asn Leu Glu
                85                  90                  95

Asn Ala Val Lys Glu Ala Asn Met Leu Val Phe Val Thr Pro His Gln
            100                 105                 110

Phe Val Glu Gly Leu Cys Lys Arg Leu Val Gly Lys Ile Lys Ala Gly
        115                 120                 125

Ala Glu Ala Leu Ser Leu Ile Lys Gly Met Glu Val Lys Arg Glu Gly
    130                 135                 140

Pro Ser Met Ile Ser Thr Leu Ile Ser Ser Leu Leu Gly Ile Asn Cys
145                 150                 155                 160

Cys Val Leu Met Gly Ala Asn Ile Ala Asn Glu Ile Ala Leu Glu Lys
                165                 170                 175

Phe Ser Glu Ala Thr Val Gly Tyr Arg Glu Asn Lys Asp Thr Ala Glu
            180                 185                 190

Lys Trp Val Arg Leu Phe Asn Thr Pro Tyr Phe Gln Val Ser Ser Val
        195                 200                 205

Gln Asp Val Glu Gly Val Glu Leu Cys Gly Thr Leu Lys Asn Val Val
    210                 215                 220

Ala Ile Ala Ala Gly Phe Val Asp Gly Leu Glu Met Gly Asn Asn Thr
225                 230                 235                 240

Lys Ala Ala Ile (2) INFORMATION FOR SEQ ID NO:13:

(i) SEQUENCE CHARACTERISTICS:
        (A) LENGTH: 574 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Cuphea lanceolata (vii) IMMEDIATE SOURCE:
        (A) LIBRARY: Genomic lambda FIX II
        (B) CLONE: C1GPDHg3

(ix) FEATURE:
        (A) NAME/KEY: CDS (B) LOCATION: 31..189

(xi) SEQUENCE DESCRIPTION: SEQ ID NO:13:

GGCATATCGA TGATTTTTCC TATCTTGCAG GGT GTC TTG ACA GCA AAA GAG GTG          54
                                 Gly Val Leu Thr Ala Lys Glu Val
                                  1               5

TAT GAG GTA CTG AAG CAC CGG GGC TGG CTC GAG CGT TTC CCG CTC TTC          102
Tyr Glu Val Leu Lys His Arg Gly Trp Leu Glu Arg Phe Pro Leu Phe
 10              15                  20

GCA ACT GTG CAT GAG ATC TCA TCT GGC AGG TTG CCT CCT TCA GCC ATT          150
Ala Thr Val His Glu Ile Ser Ser Gly Arg Leu Pro Pro Ser Ala Ile
 25              30                  35                  40

GTC AAA TAC AGC GAA CAA AAG CCC GTC TTA TCT CGA GGT TAGAACGAGA          199
Val Lys Tyr Ser Glu Gln Lys Pro Val Leu Ser Arg Gly
                 45                  50

GAAACCCGA CAAACCGGTG AAACTCGTAG TCTTAAACTG AAATCCAAAA ACATGCTGGG          259

AACATCAGCA AAAACCATTC ATCAAGGATG TCTTAGATAA AAGGTTTCAG GAAGAAATAG        319

ATGGTAGTGT GTGTAATGTT ATCAGCAATC ATTCATTCAT TTATTAAGTA TTTTTTGCAT        379

CATATTTTAT GCTAATAATT ATTACATAAA TTACTCAAAT TTTGTCAAAA TTTCTGCATT        439

GCCCCAAACA GATTAATGCA TTGAGAAAAA CTTATAAAGC TTTATCCAGC ATACATATAG       499

TTCTTTAAGC AATACAAAAA CACCCTTCTA AGCCTCTTTG AAGATGGAGT TGATCACAC        559

ATTAAAATGC TTTTT                                                         574

(2) INFORMATION FOR SEQ ID NO:14:

(i) SEQUENCE CHARACTERISTICS:
        (A) LENGTH: 53 amino acids
        (B) TYPE: amino acid
        (D) TOPOLOGY: linear (ii) MOLECULE TYPE: protein (xi) SEQUENCE DESCRIPTION: SEQ ID NO:14:

Gly Val Leu Thr Ala Lys Glu Val Tyr Glu Val Leu Lys His Arg Gly
 1               5                  10                  15

Trp Leu Glu Arg Phe Pro Leu Phe Ala Thr Val His Glu Ile Ser Ser
             20                  25                  30

Gly Arg Leu Pro Pro Ser Ala Ile Val Lys Tyr Ser Glu Gln Lys Pro
         35                  40                  45

Val Leu Ser Arg Gly
         50

(2) INFORMATION FOR SEQ ID NO:15:

(i) SEQUENCE CHARACTERISTICS:
        (A) LENGTH: 1507 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Cuphea lanceolata (vii) IMMEDIATE SOURCE:
        (A) LIBRARY: Genomic lambda FIX II
        (B) CLONE: C1GPDHg9

(ix) FEATURE:
    (A) NAME/KEY: CDS
    (B) LOCATION: 1193..1375

(xi) SEQUENCE DESCRIPTION: SEQ ID NO:15:

```
GCATGCGGGC AGGCAGGCAG GCATGGGTCT AAATTCTAGA AGACCCAGAC ATATTCATTT      60

TGTTCACAAC CGACCCATCA ATATATTGAT TAATTTTGTT TAAATTTATC ATCAGTTTTT     120

ATTTAATATT TTTAAATAGG TTTACCTTGA TCGTGATAAT TATTTAATAT TACTTTGTAA     180

TAGTTTATTT ATCTAGCGTT ATAAAATAAC ATTTGAATTC GTTGATGATA TGTGTATTTT     240

TACTATGTTT ATATGAAATT TATATTTCAA ATATTAAATA ATGTTCTTAT TTTGGCCTAT     300

GGAGAAGTAT CATCAATTTT TCTATTAAAT AACAGTCTTC AGTTTAGTCA AATCAGTTGA     360

TAAGTTCCCA AATCACACAT TGTTTGTATG AAAATTTTAA TAAAAAGTT AAGATGGTAT      420

TATTATAGAA AAATATATAA AGTATCTTTA AATAATAATT TCTTTTTAAT ACAAAAGGAA     480

ATATTTGATT ACTTGACTTA TAAAATTTAT TGATAAGGAT GCCAACTTTC ATTTTAGAAA     540

CTAGAGTAAT GATGGTTAAA TTCCCCGAAA ATGGTATGT CAATTTATTG ATACGTTCCA      600

CTACTAATTT CTGAGACATT TACATGTTTG TAAAAAAAAT CTATATATTT AAATTAAGAT     660

GGGTGTAATC AATTATAAAA TACAGCGAAT TTTAACACCG AATGAATAGA TTATCTGCAT     720

AACAATTTAT ACCATCCCTA AATACGAATT AGCAAGTTAA TAAAATTTAA TTACACGAAC     780

CATGATTATA TAAATTATCG AATCCCCGAC GTGGGGACGT ACCGAACCAA CCGTTGAAGT     840

GGTTGCCCTT TGAATCCTAA GACATACAGA CGTCATGATT CTTTGTCTCT CTATCTGTCC     900

ATTTACATAA TAAAATCAAA GAGAAGAAAA CAGAGGAAGC AGAGCATAGC ATAGCATAGC     960

ATAGAGGAGA TCGCCAGATT CAGCTGTTTC CTCATAGTTT GCCACGAGAC ATACATTGCA    1020

TTGCCCGATG CCTTTCTCCG CCTCCTTGTC CCTCTCCTCA TTCCCCCGAT GCCTTTCTCC    1080

GCCTCCTTGT CCCTCTCCTC ATTCCCTTAT ATCCCTCCTC CCCTCCCTCT TCTTCCTCTG    1140

CTCAACTCCT CCCCCTCACC CTCTTCCTCT GTTCTTCCTC TCTGCCTCTG CA ATG         1195
                                                           Met
                                                             1

GCG CCT GCC TTC GAA CCC CAT CAG CTG GTT CCT TCT GAG CTT AAC TCT      1243
Ala Pro Ala Phe Glu Pro His Gln Leu Val Pro Ser Glu Leu Asn Ser
          5                  10                  15

GCC CAC CAG AAC CCA CAT TCC AGC GGA TAT GAA GGA CCC AGA TCG AGG      1291
Ala His Gln Asn Pro His Ser Ser Gly Tyr Glu Gly Pro Arg Ser Arg
 20                  25                  30

GTC ACC GTC GTT GGC AGC GGC AAC TGG GGC AGC GTC GCT GCC AAG CTC      1339
Val Thr Val Val Gly Ser Gly Asn Trp Gly Ser Val Ala Ala Lys Leu
 35                  40                  45

ATT GCT TCC AAC ACC CTC AAG CTC CCA TCT TTC CAT GGTTAGTCTC           1385
Ile Ala Ser Asn Thr Leu Lys Leu Pro Ser Phe His
50                  55                  60

TCATTCTTCT CTCTGTAAAG TTGAAGCTTT TTCATGGAAT AGTCTCTAGA CATGAGCCCC    1445

TGTTTGCATG GTTTTGTTTT GTCTTTGAAA CATGAATAAA GGTGGTTTCT TGTGTTGGTA    1505

CC                                                                   1507
```

(2) INFORMATION FOR SEQ ID NO:16:

(i) SEQUENCE CHARACTERISTICS:
        (A) LENGTH: 61 amino acids
        (B) TYPE: amino acid
        (D) TOPOLOGY: linear (ii) MOLECULE TYPE: protein (xi) SEQUENCE DESCRIPTION: SEQ ID NO:16:

```
Met Ala Pro Ala Phe Glu Pro His Gln Leu Val Pro Ser Glu Leu Asn
 1               5                  10                  15

Ser Ala His Gln Asn Pro His Ser Ser Gly Tyr Glu Gly Pro Arg Ser
            20                  25                  30

Arg Val Thr Val Val Gly Ser Gly Asn Trp Gly Ser Val Ala Ala Lys
            35                  40                  45

Leu Ile Ala Ser Asn Thr Leu Lys Leu Pro Ser Phe His
    50                  55                  60
```

(2) INFORMATION FOR SEQ ID NO:17:

(i) SEQUENCE CHARACTERISTICS:
        (A) LENGTH: 349 amino acids
        (B) TYPE: amino acid
        (D) TOPOLOGY: linear (xi) SEQUENCE DESCRIPTION: SEQ ID NO:17:

```
Met Ala Gly Lys Lys Val Cys Ile Val Gly Ser Gly Asn Trp Gly Ser
 1               5                  10                  15

Ala Ile Ala Lys Ile Val Gly Ser Asn Ala Gly Arg Leu Ala His Phe
            20                  25                  30

Asp Pro Arg Val Thr Met Trp Val Phe Glu Glu Asp Ile Gly Gly Arg
            35                  40                  45

Lys Leu Thr Glu Ile Ile Asn Thr Gln His Glu Asn Val Lys Tyr Leu
    50                  55                  60

Pro Gly His Lys Leu Pro Pro Asn Val Val Ala Ile Pro Asp Val Val
65                  70                  75                  80

Gln Ala Ala Thr Gly Ala Asp Ile Leu Val Phe Val Val Pro His Gln
                85                  90                  95

Phe Ile Gly Lys Ile Cys Asp Gln Leu Lys Gly His Leu Lys Ala Asn
            100                 105                 110

Thr Ile Gly Ile Ser Leu Ile Lys Gly Val Asp Glu Gly Pro Asn Gly
            115                 120                 125

Leu Lys Leu Ile Ser Glu Val Ile Gly Glu Arg Leu Gly Ile Pro Met
130                 135                 140

Ser Val Leu Met Gly Ala Asn Ile Ala Ser Glu Val Ala Glu Glu Lys
145                 150                 155                 160

Phe Cys Glu Thr Thr Ile Gly Cys Lys Asp Pro Ala Gln Gly Gln Leu
                165                 170                 175

Leu Lys Asp Leu Met Gln Thr Pro Asn Phe Arg Ile Thr Val Val Gln
            180                 185                 190

Glu Val Asp Thr Val Glu Ile Cys Gly Ala Leu Lys Asn Ile Val Ala
            195                 200                 205

Val Gly Ala Gly Phe Cys Asp Gly Leu Gly Phe Gly Asp Asn Thr Lys
210                 215                 220

Ala Ala Val Ile Arg Leu Gly Leu Met Glu Met Ile Ala Phe Ala Lys
225                 230                 235                 240

Leu Phe Cys Ser Gly Thr Val Ser Ser Ala Thr Phe Leu Glu Ser Cys
                245                 250                 255

Gly Val Ala Asp Leu Ile Thr Thr Cys Tyr Gly Gly Arg Asn Arg Lys
            260                 265                 270

Val Ala Glu Ala Phe Ala Arg Thr Gly Lys Ser Ile Glu Gln Leu Glu
            275                 280                 285
```

```
Lys Glu Met Leu Asn Gly Gln Lys Leu Gln Gly Pro Gln Thr Ala Arg
    290                 295                 300

Glu Leu His Ser Ile Leu Gln His Lys Gly Leu Val Asp Lys Phe Pro
305                 310                 315                 320

Leu Phe Thr Ala Val Tyr Lys Val Cys Tyr Glu Gly Gln Pro Val Gly
                325                 330                 335

Glu Phe Ile Arg Cys Leu Gln Asn His Pro Glu His Met
            340                 345
```